(12) United States Patent
Wang et al.

(10) Patent No.: US 8,454,512 B2
(45) Date of Patent: Jun. 4, 2013

(54) CONFOCAL PHOTOACOUSTIC MICROSCOPY WITH OPTICAL LATERAL RESOLUTION

(75) Inventors: Lihong Wang, Creve Coeur, MO (US); Konstantin Maslov, Affton, MO (US)

(73) Assignee: Washington University, St. Louis, MO (US)

( * ) Notice: Subject to any disclaimer, the term of this patent is extended or adjusted under 35 U.S.C. 154(b) by 324 days.

(21) Appl. No.: 12/739,589

(22) PCT Filed: Oct. 24, 2008

(86) PCT No.: PCT/US2008/081167
§ 371 (c)(1), (2), (4) Date: Jun. 28, 2010

(87) PCT Pub. No.: WO2009/055705
PCT Pub. Date: Apr. 30, 2009

(65) Prior Publication Data
US 2010/0268042 A1    Oct. 21, 2010

(51) Int. Cl.
*A61B 8/00* (2006.01)

(52) U.S. Cl.
USPC .......................... 600/437; 600/459; 600/476

(58) Field of Classification Search
USPC .................................................. 600/437–480
See application file for complete search history.

(56) References Cited

U.S. PATENT DOCUMENTS

| | | | |
|---|---|---|---|
| 4,255,971 A | 3/1981 | Rosencwaig | |
| 4,267,732 A | 5/1981 | Quate | |
| 4,468,136 A | 8/1984 | Murphy et al. | |
| 5,718,231 A | 2/1998 | Dewhurst et al. | |
| 5,840,023 A * | 11/1998 | Oraevsky et al. | 600/407 |
| 6,498,942 B1 * | 12/2002 | Esenaliev et al. | 600/310 |
| 6,498,945 B1 * | 12/2002 | Alfheim et al. | 600/407 |
| 7,198,778 B2 | 4/2007 | Achilefu et al. | |
| 8,016,419 B2 * | 9/2011 | Zhang et al. | 351/206 |
| 8,025,406 B2 * | 9/2011 | Zhang et al. | 351/219 |
| 2006/0181791 A1 * | 8/2006 | Van Beek et al. | 359/845 |
| 2006/0184042 A1 * | 8/2006 | Wang et al. | 600/476 |
| 2010/0245766 A1 * | 9/2010 | Zhang et al. | 351/206 |
| 2010/0245769 A1 * | 9/2010 | Zhang et al. | 351/219 |
| 2010/0245770 A1 * | 9/2010 | Zhang et al. | 351/219 |
| 2010/0249562 A1 * | 9/2010 | Zhang et al. | 600/365 |
| 2010/0309466 A1 * | 12/2010 | Lucassen et al. | 356/303 |
| 2011/0201914 A1 * | 8/2011 | Wang et al. | 600/407 |
| 2011/0282181 A1 * | 11/2011 | Wang et al. | 600/407 |
| 2011/0282192 A1 * | 11/2011 | Axelrod et al. | 600/427 |

OTHER PUBLICATIONS

Cheong et al., "A review of the optical properties of biological tissues", IEEE J. Quantum Electronics, 1990, pp. 2166-2185, vol. 26.

(Continued)

*Primary Examiner* — Sanjay Cattungal
(74) *Attorney, Agent, or Firm* — Armstrong Teasdale LLP

(57) ABSTRACT

A confocal photoacoustic microscopy system includes a laser configured to emit a light pulse, a focusing assembly configured to receive the light pulse and to focus the light pulse into an area inside an object, an ultrasonic transducer configured to receive acoustic waves emitted by the object in response to the light pulse, and an electronic system configured to process the acoustic waves and to generate an image of the area inside the object. The focusing assembly is further configured to focus the light pulse on the object in such a way that a focal point of the focusing assembly coincides with a focal point of the at least one ultrasonic transducer.

18 Claims, 16 Drawing Sheets

1. Condenser lens
2. Pinhole
3. Objective lens
4. Ultrasonic transducer
5. Correcting lens
6. Isosceles prism
7. Rhomboidal prism
8. Acoustic lens
9. Silicon oil layer
10. Beam splitter
11. Photo-detector
12. Aligning optics
13. Object

OTHER PUBLICATIONS

Guittet et al., "In vivo high-frequency ultrasonic characterization of human dermis", 1999, IEEE Trans. Biomed. Eng., pp. 740-746, vol. 46.

Hoelen et al., "Three-dimensional photoacoustic imaging of blood vessels in tissue", 1998, Opt. Lett., pp. 648-650, vol. 23.

Kolkman et al., "In vivo photoacoustic imaging of blood vessels using an extreme-narrow aperture sensor", IEEE Journal on Selected Topics in Quantum Electronics, 2003, pp. 343-346, vol. 9.

Maslov et al., "In vivo dark-field reflection-mode photoacoustic microscopy", 2005, Optical Letters, pp. 625-627, vol. 30.

Nakajima et al., "Three-dimensional analysis and classification of arteries in the skin and subcutaneous adipofascial tissue by computer graphics imaging", 1998, Plastic and Reconstructive Surgery, pp. 749-760, vol. 102.

Nelson et al., "Imaging gliblastoma multiforme", 2003, Cancer J., pp. 134-146, vol. 9.

Oraevsky et al., "Laser opto-acoustic imaging of the breast: detection of cancer angiogenesis", 1999, Proc. SPIE, pp. 352-363, vol. 3597.

Potter et al., Capillary diameter and geometry in cardiac and skeletal muscle studied by means of corrosion casts, 1983, Microvascular Research, pp. 68-84, vol. 25.

Savateeva et al., Noninvasive detection and staging of oral cancer in vivo with confocal optoacoustic tomography, 2000, Proceedings of SPIE, pp. 55-66, vol. 3916.

Zhang et al., "Functional photoacoustic microscopy for high-resolution and noninvasive in vivo imaging", 2006, Nature Biotechnology, pp. 848-851, vol. 24.

Zharov et al., "In vivo photoacoustic flow cytometry for monitor of circulating single cancer cells and contrast agents", 2006, Optics Letters, pp. 3623-3625, vol. 31.

Written Opinion and International Search Report for PCT/US2008/081167, dated Apr. 22, 2009, 7 pages.

Zhang et al., "In vivo imaging of subcutaneous structures using functional photoacoustic microscopy", Nature Protocols, 2007, pp. 797-804, vol. 2, No. 4.

\* cited by examiner

1. Objective lenses
2. Ultrasonic transducer
3. Correcting lens
4. Right-angle prism
5. Acoustic lens
6. Metal coating
7. Single mode fiber
8. Beam splitter
9. Photo-detector
10. Aligning optics
11. Object 1. Single mode fiber
2. Sampling mirror
3. Reference photodiode
4. Objective lens
5. Ultrasonic transducer
6. Pendulum
7. Pivot
8. Frame
9. Actuator
10. Position sensor
11. Membrane 1. Single mode fiber
2. Flexible shaft
3. Catheter
4. Objective lens
5. Prism
6. Ultrasonic transducer
7. Acoustically an optically transparent window

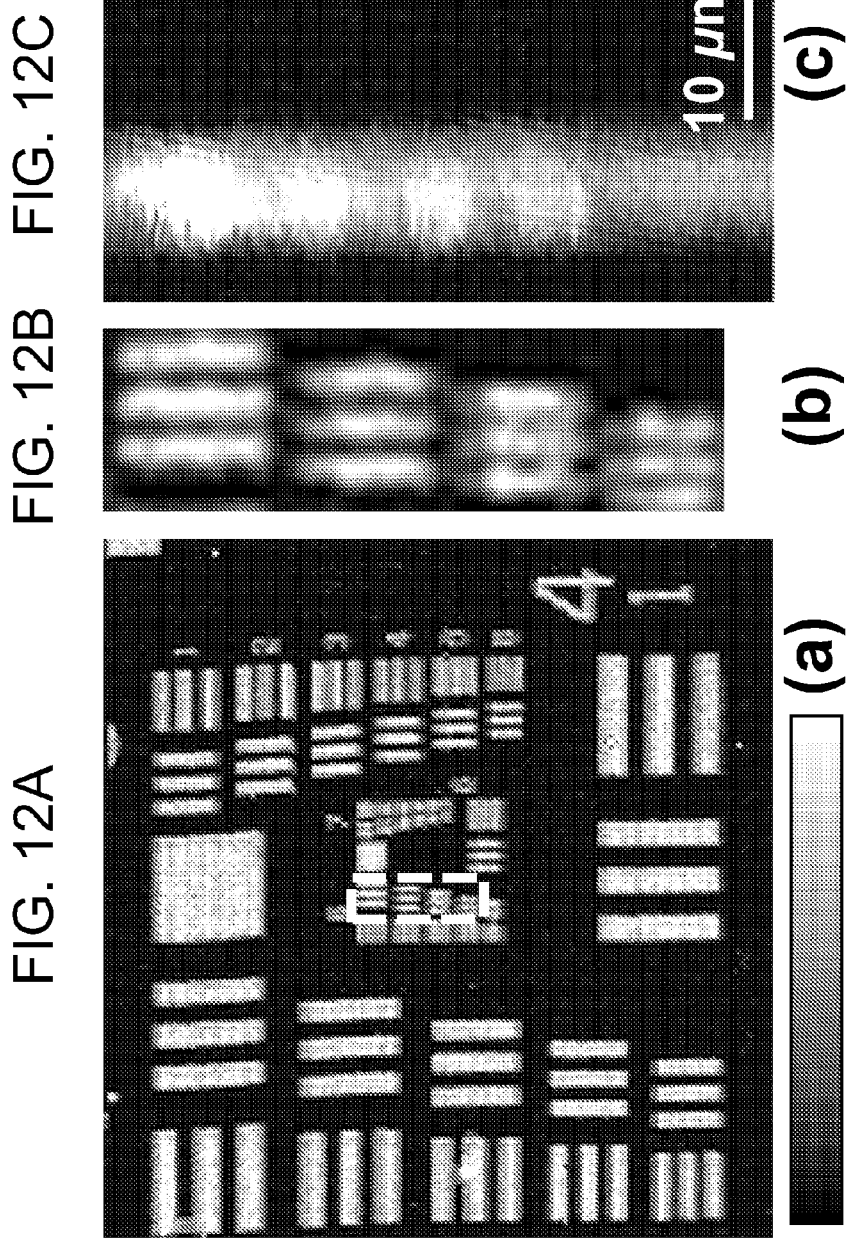

−100 μm

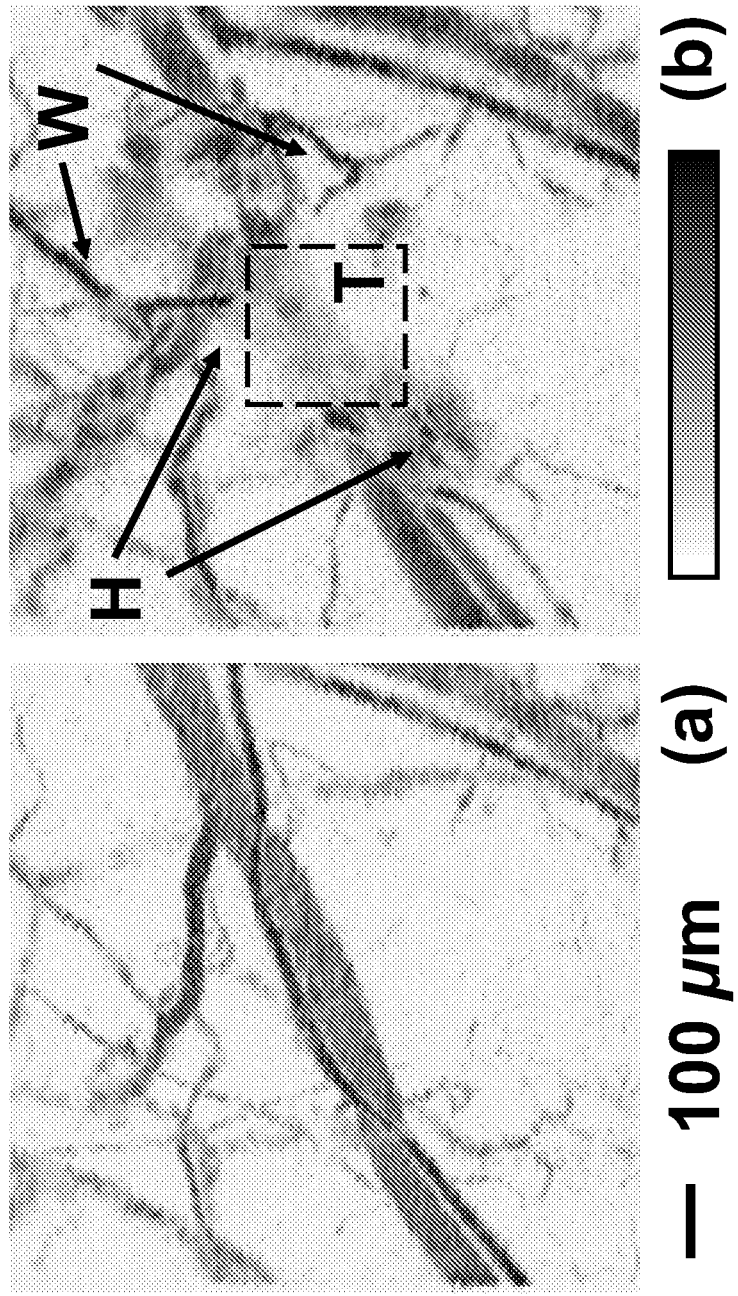

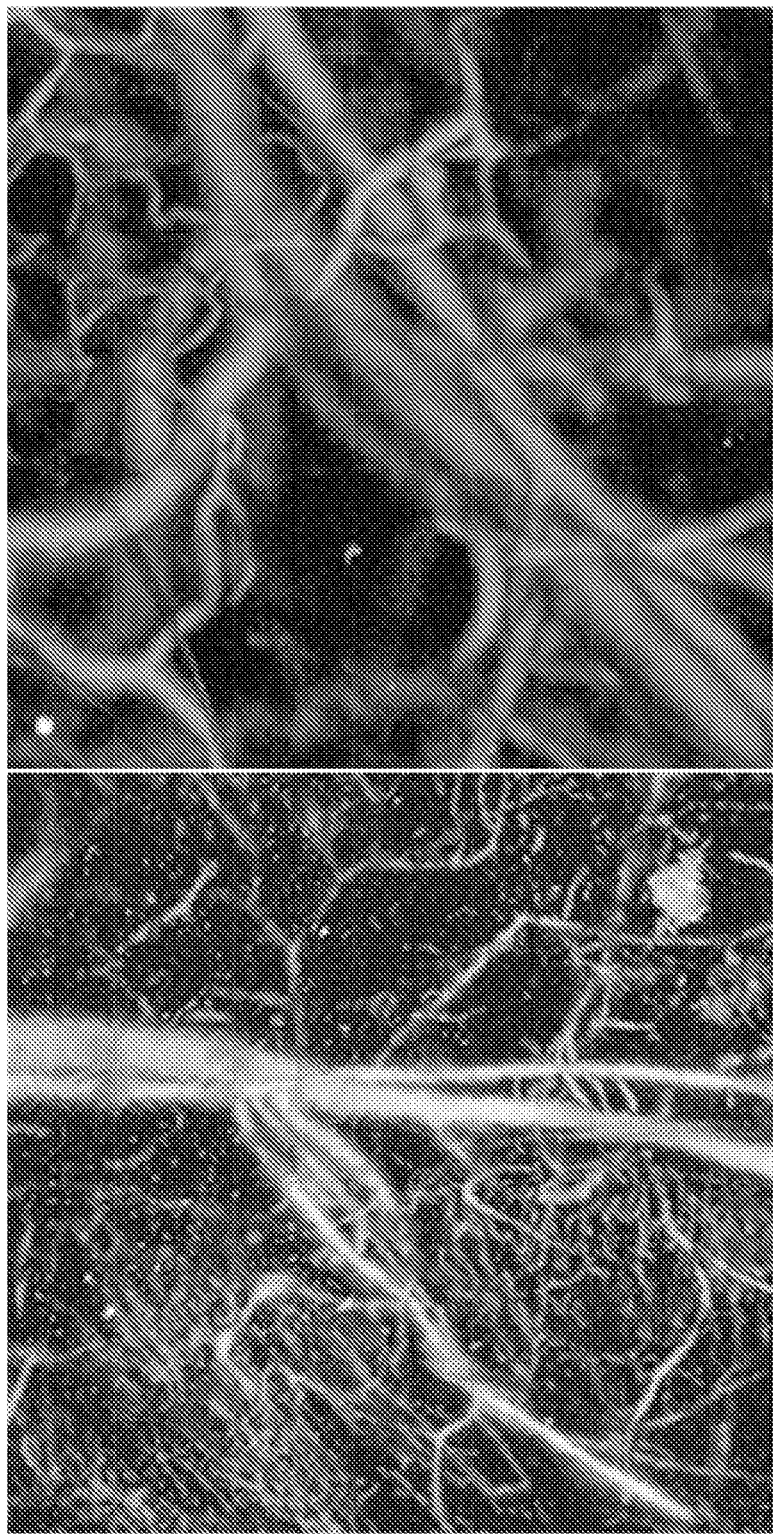

CONFOCAL PHOTOACOUSTIC MICROSCOPY WITH OPTICAL LATERAL RESOLUTION

STATEMENT REGARDING FEDERALLY SPONSORED RESEARCH & DEVELOPMENT

This invention was made with government support under grants R01 EB000712 and R01 NS46214, both awarded by the U.S. National Institutes of Health. The government has certain rights in the invention.

CROSS REFERENCE TO RELATED APPLICATIONS

This application is a U.S. National Phase Patent Application of International Application Serial Number PCT/US2008/081167 filed Oct. 24, 2008, which is incorporated herein in its entirety, and which claims priority from U.S. Provisional Patent Application 60/982,624 filed Oct. 25, 2007, which is incorporated herein in its entirety.

BACKGROUND

The field of the invention relates generally to noninvasive imaging and, more particularly, to imaging an area with an object using confocal photoacoustic imaging.

The capability of noninvasively imaging capillaries, the smallest blood vessels, in vivo has long been desired by biologists at least because it provides a window to study fundamental physiological phenomena, such as neurovascular coupling, on a microscopic level. Existing imaging modalities, however, are unable to simultaneously provide sensitivity, contrast, and spatial resolution sufficient to noninvasively image capillaries.

BRIEF DESCRIPTION

In one aspect, a method for noninvasively imaging a scattering medium is provided. The method includes focusing a light pulse into a predetermined area inside an object using a focusing assembly, and transforming a photoacoustic signal into an acoustic wave, wherein the photoacoustic signal is emitted by the object in response to the light pulse. The method also includes detecting the acoustic wave using a transducer that is positioned such that the transducer and the focusing assembly are coaxial and confocal, and creating an image of the predetermined area inside the object based on a signal generated by the transducer representative of the acoustic wave.

In another aspect, a confocal photoacoustic imaging apparatus is provided. The apparatus includes a focusing assembly configured to receive a light pulse and to focus the light pulse into an area inside an object, a transducer configured to receive acoustic waves emitted by the object in response to the light pulse, wherein the transducer is positioned such that the transducer and the focusing assembly are coaxial. The apparatus also includes a processor configured to record and process the received acoustic waves.

In another aspect, a confocal photoacoustic microscopy system is provided, including a laser configured to emit a light pulse, a focusing assembly configured to receive the at least one light pulse and to focus the light pulse into an area inside an object, an ultrasonic transducer configured to receive acoustic waves emitted by the object in response to the light pulse, and an electronic system configured to process the acoustic waves and to generate an image of the area inside the object. The focusing assembly is further configured to focus the light pulse on the object in such a way that a focal point of the focusing assembly coincides with a focal point of the ultrasonic transducer.

BRIEF DESCRIPTION OF THE DRAWINGS

Aspects of the invention may be better understood by referring to the following description in conjunction with the accompanying drawings.

FIGS. 12A-12C are images representing a lateral resolution measurement by the imaging system using a resolution test target immersed in clear liquid.

FIGS. 15A and 15B are maximum amplitude projection (MAP) images acquired before and after a high-intensity laser treatment.

FIG. 16A is an in vivo image of a capillary bed captured using the imaging system.

FIG. 16B is an in vivo image of multiple levels of blood vessel bifurcations captured using the imaging system.

DETAILED DESCRIPTION

Figure 1:
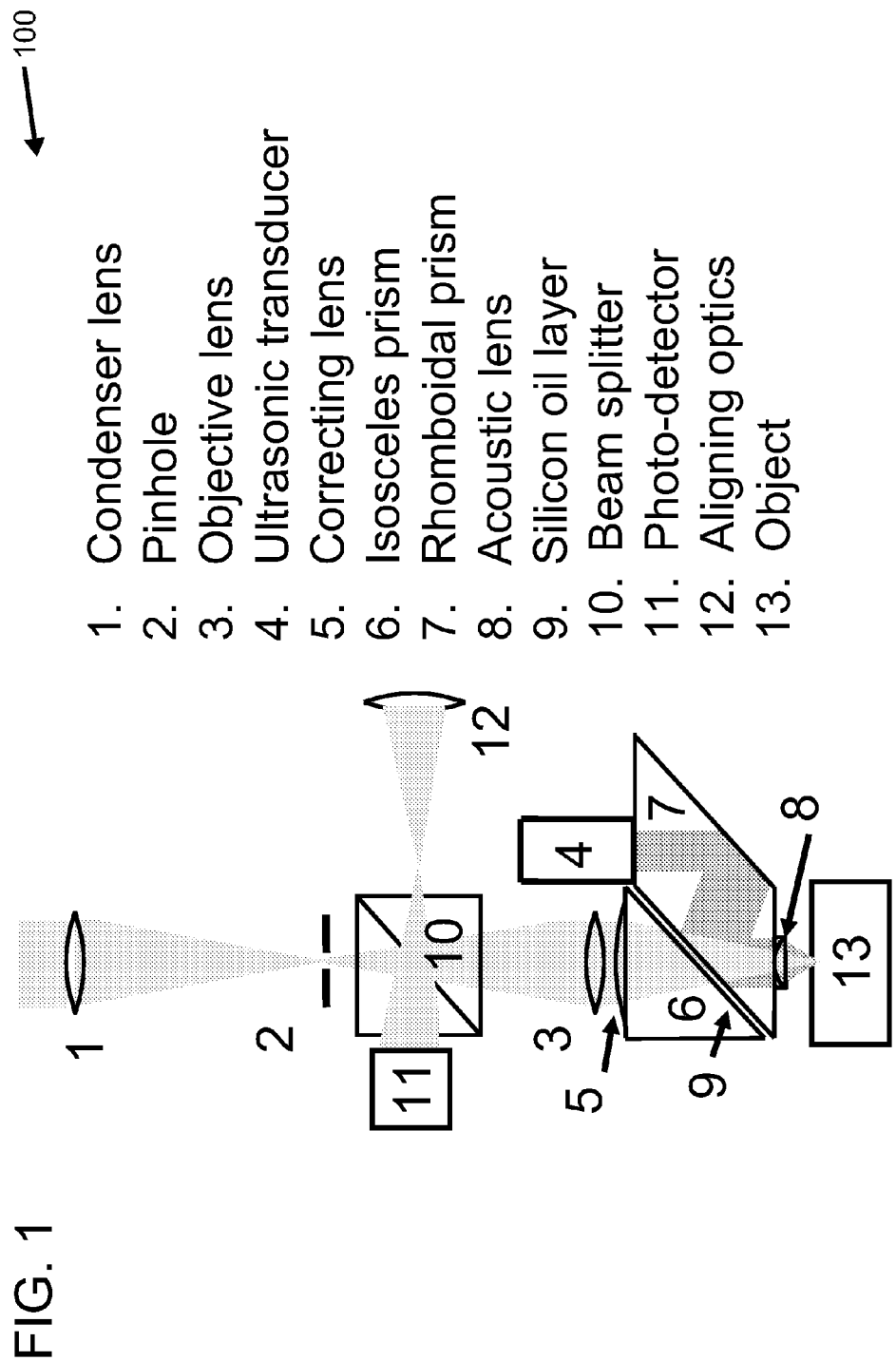
FIG. 1 is a diagram of a photoacoustic sensor that may be used with an imaging system.

While the making and using of various embodiments of the invention are discussed in detail below, it should be appreciated that the presently described embodiments provide many applicable inventive concepts that may be embodied in a wide variety of contexts. The embodiments discussed herein are merely illustrative of exemplary ways to make and use embodiments of the invention and do not delimit the scope of the invention.

To facilitate the understanding of the presently described embodiments, a number of terms are defined below. Terms defined herein have meanings as commonly understood by a person of ordinary skill in the areas relevant to aspects of the invention. Terms such as "a," "an," "the," and "said" are not intended to refer to only a singular entity, but include the general class of which a specific example may be used for illustration and are intended to mean that there are one or more of the elements. The terms "comprising," "including," and "having" are intended to be inclusive and mean that there may be additional elements other than the listed elements.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

The terminology herein is used to describe embodiments of the invention, but their usage does not delimit the invention.

In embodiments of the invention, the terms used herein follow the definitions recommended by the Optical Society of America (OCIS codes).

In embodiments of the invention, the term "photoacoustic microscopy" includes, but is not limited to, a photoacoustic imaging technology that detects pressure waves generated by light absorption in the volume of a material, such as, but not limited to biological tissue, and propagated to the surface of the material. Photoacoustic microscopy includes, but is not limited to, a method for obtaining images of the optical contrast of a material by detecting acoustic and/or pressure waves traveling from an object under investigation. Moreover, the term "photoacoustic microscopy" includes, but is not limited to, detection of the pressure waves that are still within the object.

In embodiments of the invention, the term "photoacoustic tomography" includes, but is not limited to, a photoacoustic imaging technology that detects acoustic and/or pressure waves generated by light absorption in the volume of a material, such as, but not limited to biological tissue, and propagated to the surface of the material.

In embodiments of the invention, the term "piezoelectric detectors" includes, but is not limited to, detectors of acoustic waves utilizing the principle of electric charge generation upon a change of volume within crystals subjected to a pressure wave.

In embodiments of the invention, the terms "reflection mode" and "transmission mode" includes, but is not limited to, a laser photoacoustic microscopy system that employs the detection of acoustic and/or pressure waves transmitted from a volume from which the waves are generated to an optically irradiated surface and a surface that is opposite to, or substantially different from, the irradiated surface, respectively.

In embodiments of the invention, the term "time-resolved detection" includes, but is not limited to, the recording of the time history of a pressure wave with a temporal resolution sufficient to reconstruct the pressure wave profile.

In embodiments of the invention, the term "transducer array" includes, but is not limited to, an array of ultrasonic transducers.

In embodiments of the invention, the terms "focused ultrasonic detector," "focused ultrasonic transducer," and "focused piezoelectric transducer" include, but are not limited to, a curved ultrasonic transducer with a hemispherical surface or a planar ultrasonic transducer with an acoustic lens attached or an electronically focused ultrasonic array transducer.

In embodiments of the invention, the term "diffraction-limited focus" includes, but is not limited to, a best possible focusing of light within limitations imposed by diffraction.

In embodiments of the invention, the term "confocal" includes, but is not limited to, a situation when the focus of the illumination system coincides with the focus of the detection system.

The embodiments described herein relate to noninvasively imaging capillaries. Some of the embodiments relate to microscopic photoacoustic imaging using focused optical illumination and focused ultrasonic detection. For example, an embodiment performs optical-resolution photoacoustic microscopy (OR-PAM), which facilitates providing a lateral resolution of 5 micrometers ($\mu$m) and a maximum imaging depth of greater than 0.7 millimeters (mm) based on endogenous optical absorption contrast. In vivo images of healthy capillary networks and laser coagulated microvessels in mouse ears, for example, are demonstrated as examples of applications of OR-PAM in biomedical research.

In an embodiment, the lateral resolution is dominantly determined by the optical focus. A tightly focused optical illumination produces a local temperature rise due to light absorption. The temperature rise leads to thermal expansion, which results in photoacoustic emission. The photoacoustic emission may be detected by a high-frequency large numerical-aperture spherically focused ultrasonic transducer that is coaxial and confocal with the light focusing system. The photoacoustic emission may also be measured by an ultrasonic transducer array, a phase sensitive optical coherence tomography apparatus, a laser optical interferometer, and/or a capacitive surface displacement sensor. By focusing light to a focal spot of several micrometers in diameter, embodiments of the invention significantly improve the image resolution of photoacoustic microscopy of biological tissue or other optically scattering media. It combines the high spatial resolution of optical confocal microscopy and the high optical absorption contrast of photoacoustic tomography.

The embodiments described herein provide for reflection-mode microscopic photoacoustic imaging using focused optical illumination. Embodiments of the invention use a nearly diffraction-limited focused optical illumination to achieve high spatial resolution. Embodiments of the invention use a confocal arrangement between the optical focus and the ultrasonic focus of a high-frequency large numerical-aperture (NA) spherically focused ultrasonic transducer to achieve high sensitivity. The ultrasonic transducer may be replaced with another detector capable of measuring local thermal expansion. By tightly focusing light, the lateral resolution limitations of existing photoacoustic microscopy based on the resolution of the ultrasonic focusing system may be overcome. In addition, because a photoacoustic signal is proportional to the optical fluence at the target, the currently described embodiments require only a low laser pulse energy and, hence, may be made relatively compact, fast, and inexpensive. In the exemplary embodiment, a laser pulse energy of approximately 100 nanojoules (nJ) may be used.

Moreover, exemplary embodiments utilize optical focusing and time-resolved detection of laser-induced pressure waves to obtain three-dimensional images of the distribution of optical-absorption contrast within a sampling volume. The exemplary embodiments provide non-invasive imaging of scattering media, such as, but not limited to, biological tissue in vivo. The exemplary embodiments provide non-invasive imaging up to approximately one optical transport mean free path deep. For most biological tissue, an optical transport mean free path is approximately 1.0 millimeter (mm). In the exemplary embodiment, resolution on the order of 1.0 micrometer (μm) is attainable. Further, the exemplary embodiment images optical-absorption contrast in biological tissue up to approximately 0.7 mm deep with a lateral resolution of approximately 5.0 μm. In embodiments of the invention, a large numerical-aperture (NA) spherically focused ultrasonic transducer is used in a confocal coaxial arrangement with the light focusing optics to facilitate providing high axial resolution of between 10.0 and 15.0 μm.

An imaging procedure, which uses a confocal photoacoustic imaging system, is one of the possible embodiments and is aimed at medical and biological applications. The presently described embodiments are complementary to the structural information that may be obtained from pure optical and ultrasonic imaging technologies and may be used for diagnostic, monitoring or research purposes. Applications of the technology include, but are not limited to, the imaging of arteries, veins, capillaries (the smallest blood vessels), pigmented tumors such as melanomas, and sebaceous glands in vivo in humans or animals. The presently described embodiments may use the spectral properties of intrinsic optical contrast to monitor blood oxygenation (oxygen saturation of hemoglobin), blood volume (total hemoglobin concentration), and even the metabolic rate of oxygen consumption; it may also use the spectral properties of a variety of dyes or other contrast agents to obtain additional functional or molecular-specific information. In other words, the presently described embodiments are capable of functional and molecular imaging. Further, the presently described embodiments may be used to monitor possible tissue changes during x-ray radiation therapy, chemotherapy, or other treatment. In addition, presently described embodiments may also be used to monitor topical application of cosmetics, skin creams, sun-blocks or other skin treatment products. The presently described embodiments, when miniaturized, may also be used endoscopically, e.g., for the imaging of atherosclerotic lesions in blood vessels.

Further, the presently described embodiments provide a method of characterizing a target within a tissue by focusing one or more laser pulses on the region of interest in the tissue so as to penetrate the tissue and illuminate the region of interest, receiving the pressure waves induced in the object by optical absorption using one or more ultrasonic transducers that are focused on the same region of interest, and recording the received acoustic waves so that the structure or composition of the object may be imaged. The one or more laser pulses are focused by a microscope objective lens or a similar tightly focusing optical system, which typically includes an optical assembly of lenses and/or mirrors, which converges the one or more laser pulses towards the focal point of the ultrasonic transducer. The focusing device may also use one or more optical spatial filters, which may be a diaphragm or a single-mode fiber, to reduce the focal spot of the optical system to the smallest possible size so that the highest possible spatial resolution may be achieved. The focused one or more laser pulses selectively heat the region of interest, causing the object to expand and produce a pressure wave whose temporal profile reflects the optical absorption and thermo-mechanical properties of the target. Alternatively, an annular array of ultrasonic transducers may be used along the tissue to enhance a depth of field of an imaging system by using synthetic aperture image reconstruction. The signal recording includes digitizing the received acoustic waves and transferring the digitized acoustic waves to a computer for analysis. The image of the object is formed from the recorded acoustic waves.

In addition, the presently described embodiments may also include an electronic system in communication with the focusing device, the one or more ultrasonic transducers, or a combination thereof. In one embodiment, the electronic system includes an XYZ or circular scanner or scanners, an amplifier, a digitizer, a laser wavelength tuning electronics, a computer, a processor, a display, a storage device, or combination thereof. One or more component of the electronic system may be in communication remotely with the other components of the electronic system, the apparatus, or both.

FIG. 1 shows a schematic of an exemplary focusing assembly 100 which uses the confocal photoacoustic microscopy method. The light out of the dye laser is focused by a condenser lens 1 on a diaphragm (pinhole) 2 for spatial filtering. Sampling beam splitter 10 is used to monitor the laser output power through photo-detector 11 and to optically image the object surface through eyepiece or aligning optics 12 for alignment. The light coming out of the spatial filter is focused by microscope objective lens 3 onto object 13 through beam separating element 6, 7, 9, and acoustic lens 8. Correction lens 5 placed on top of the beam separation element compensates for the aberrations introduced by the prisms and the acoustic lens. The distance between the pinhole and the objective lens is approximately 400 millimeters (mm), which gives an optical focusing spot size of approximately 3.7 micrometers (μm) in diameter and a focal zone of approximately 200 μm in water. The laser pulse energy measured after the objective lens is approximately 100 nanojoules (nJ). The beam separation element consists of an isosceles triangular prism 6 with an apex angle of approximately 52.5° and a rhomboidal 52.5° prism 7. Prisms 6 and 7 are adjoined along the diagonal surfaces with a gap of approximately 0.1 mm in between. Gap 9 is filled with an optical refractive-index-matching, low-acoustic-impedance, nonvolatile liquid such as 1000 cSt silicone oil, commercially available from Clearco Products. The silicone oil and the glass have a good optical refractive index match (glass: 1.5; silicone oil: 1.4) but a large acoustic impedance mismatch (glass: 12.1×106 N·s/m3; silicone oil: 0.95× 106 N·s/m3). As a result, the silicone oil layer is optically transparent but acted as an acoustic reflector. The photoacoustic signal emitted by the target is transformed by the acoustic lens, having a radius of curvature of approximately 5.2 mm, a diameter of approximately 6.35 mm, a NA of approximately 0.46 in water, and an ultrasonic focal spot size of approximately 27 μm, into a plane elastic wave in rhomboidal prism 7 and is then detected by the high-frequency direct-contact ultrasonic transducer 4 such as a model V2012-BC transducer, commercially available from Panametrics-NDT with a center frequency of approximately 75 MHz, a bandwidth of approximately 80%, and an active element diameter of approximately 6.35 mm. Within the bandwidth of the ultrasonic transducer 4, ultrasonic absorption in silicone oil is high enough to dampen ultrasonic reverberations in the matching layer and thus minimize interferences to the image.

Figure 2:
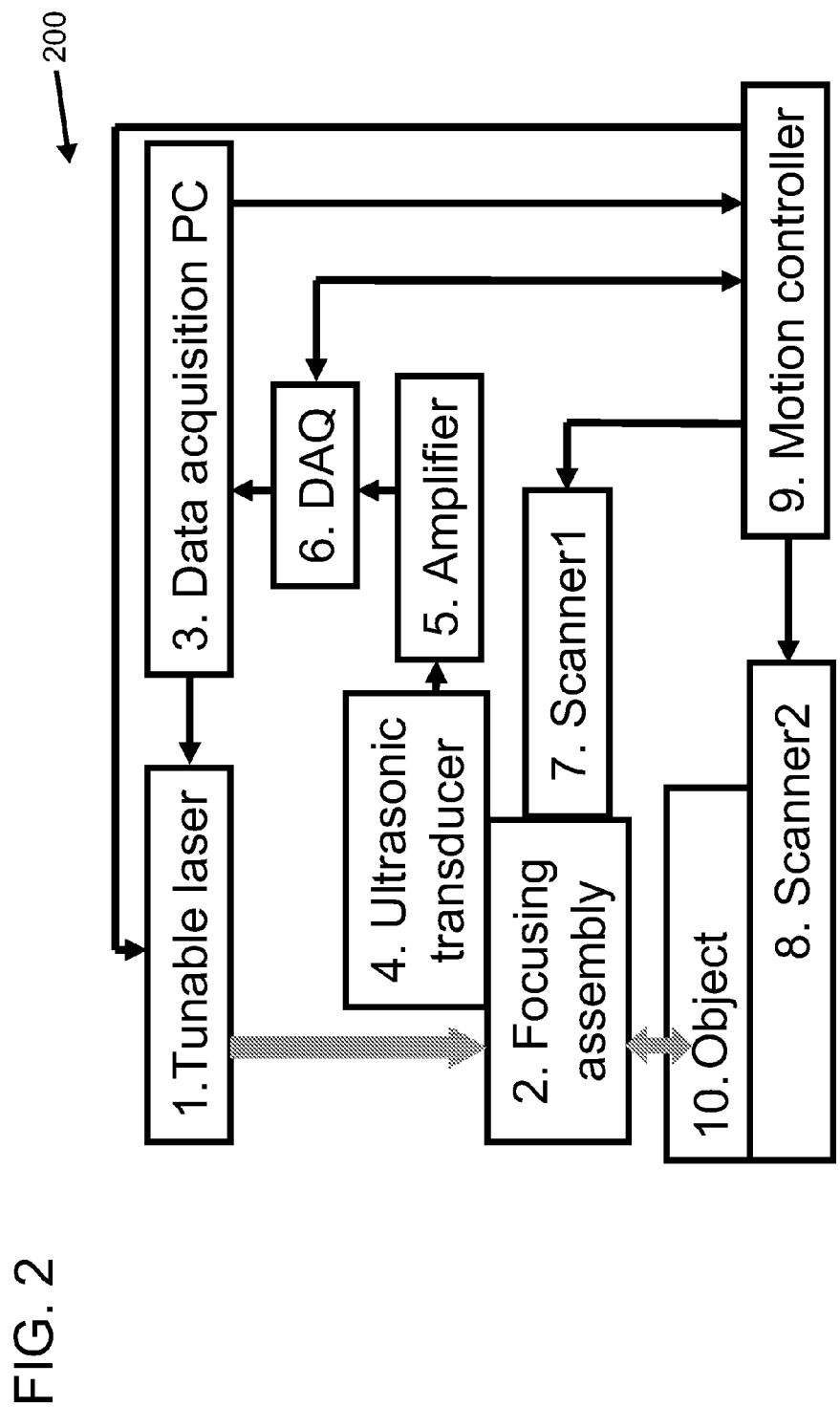
FIG. 2 is a block diagram of a system that uses confocal photoacoustic microscopy.

FIG. 2 is a block diagram of a system 200 based on confocal photoacoustic microscopy, which is capable of contour scanning and quantitative spectroscopic measurement. The system includes a pulsed tunable laser 1 including a tunable laser pumped by a Q-switched laser, a focusing assembly 2, one or more ultrasonic transducers 4, and an electronic system. The electronic system includes data acquisition personal computer (PC) 3, motion controller 9, first and second scanners 7 and 8, amplifier 5, and data acquisition subsystem (DAQ) 6, which includes a signal conditioner and a digitizer.

Focusing assembly 2 receives one or more laser pulses and focuses the one or more laser pulses into an area inside the sample object 10 so as to penetrate the tissue and illuminate the region of interest. The one or more ultrasonic transducers 4 are focused on the same the region of interest and receive the acoustic or pressure waves induced in the region of interest by the one or more laser pulses. The electronic system records and processes the received acoustic or pressure waves. The laser pulse generation, data acquisition, and object scanning are synchronized with the pulses produced by the motor controller at programmed locations of the laser focus with respect to object 10. As described above, the focusing assembly 2 includes an optical assembly of lenses and/or mirrors that focuses one or more laser beams on the object in such a way that the focal point of the optical focusing device coincides with that of the one or more ultrasonic transducers.

The focusing assembly is placed on an XYZ translation stage to perform raster scanning along the object surface with simultaneous adjustment of the sensor's axial position to compensate for the curvature of the object surface. Other embodiments may use different ways of image formation, which include, but are not limited to, circular scanning, sector scanning, optical scanning, electronic focusing a transducer array, and array-based image reconstruction. The recorded pressure-wave time histories are displayed by the computer versus the focusing assembly position to construct a three dimensional image of the distribution of the optical contrast within the tissue, i.e., a three dimensional tomographic image of the object.

System 200 employs a tunable dye laser, such as a model CBR-D laser, commercially available from Sirah, pumped by a neodymium-doped yttrium lithium fluoride (Nd:YLF) laser, such as the INNOSLAB laser, commercially available from Edgewave, as the irradiation source. The laser pulse duration is approximately 7 nanoseconds (ns) and the pulse repetition rate, which is controlled by the external triggering signal, is as high as approximately 2 kilohertz (kHz). In alternative embodiments, a plurality of sources of penetrating radiation, which may be confined to or concentrated in a small volume within the object, may be used. Such sources include, but are not limited to, pulsed lasers, flash lamps, other pulsed electromagnetic sources, particle beams, or their intensity-modulated continuous-wave counterparts.

The one or more focused short laser pulses are delivered to an object (e.g., human or animal body, tissue or organ) under investigation, where a small area of the object inside the focal area of the ultrasonic transducer is illuminated. The laser wavelength is selected as a compromise between the desired light penetration depth and the contrast between the structures of interest and the surrounding medium. Light absorption by the internal structures causes a transient temperature rise which, due to thermoelastic expansion of the medium, produces elastic waves that may travel through the medium.

High-frequency ultrasonic waves generated in tissue by the laser pulse are recorded and analyzed by a PC to form a three-dimensional image. The shape and dimensions of the optical-contrast structures are generally determined from the temporal profile of the laser-induced ultrasonic waves and the position of the focusing assembly. Ordinarily, a raster scan by the focusing assembly is used to form a three-dimensional image. However, a transducer array may be used to reduce the time of scanning and the total light exposure. When the tissue under investigation is an internal organ, the optical fiber and ultrasonic transducer may be incorporated in an endoscope and positioned inside the body. The following examples will be provided for the purpose of illustrating various embodiments of the invention and are not meant to limit the present invention in any fashion.

As illustrated in FIGS. 3-6, the presently described embodiments provide an optical resolution confocal microscopic photoacoustic imaging technology to image biological tissues in vivo. The exemplary embodiment has a lateral resolution as high as approximately 5 μm and a maximum imaging depth of approximately 0.7 mm. In alternative embodiments, the image resolution may be further improved by increasing the frequency of the ultrasonic transducer and the numerical aperture of the optical objective lens perhaps at the cost of imaging depth. The photoacoustic images shown in FIGS. 12-16 were obtained with minimal signal averaging and, therefore, could be further improved by averaging, at the expense of data acquisition time, in another embodiment of the invention. The current imaging speed is limited by the pulse repetition rate of the laser. Because lasers with pulse repetition rates of up to 100 KHz are now available, other embodiments involve faster photoacoustic imaging, which can reduce motion artifacts, and extensive signal averaging.

The presently described embodiments include any realization of light focusing any kind of mirrors, lenses, fibers, and diaphragms that may produce well focused (preferably diffraction-limited) illumination confined to the focal area of the focused ultrasonic transducer. The presently described embodiments also cover any confocal photoacoustic techniques with any light delivery and detection arrangements in which the lateral resolution is defined by the focusing of the incident radiation rather than the acoustic detection unit.

One or more of the following embodiments may be used to implement laser focusing for the purpose described herein: (1) an optical microscope objective lens that focuses a well-collimated single-mode lased beam into a nearly diffraction-limited point, (2) an objective lens that forms an image of a small pinhole on the region of interest, (3) a focusing system in which a single-mode optical fiber is used instead of pinhole, (4) a focusing system in which an oscillating mirror scans the optical focus rapidly within the larger focal area of the ultrasonic transducer. The following embodiments, and further alternative embodiments, may also be used to implement laser focusing for further, undescribed purposes. Various examples of the focusing assembly will now be described in reference to FIGS. 3-10, wherein the focusing assembly includes, for example, an optical focusing device, and one or more ultrasonic transducers in the piezoelectric, optical, or another form.

Figure 3:
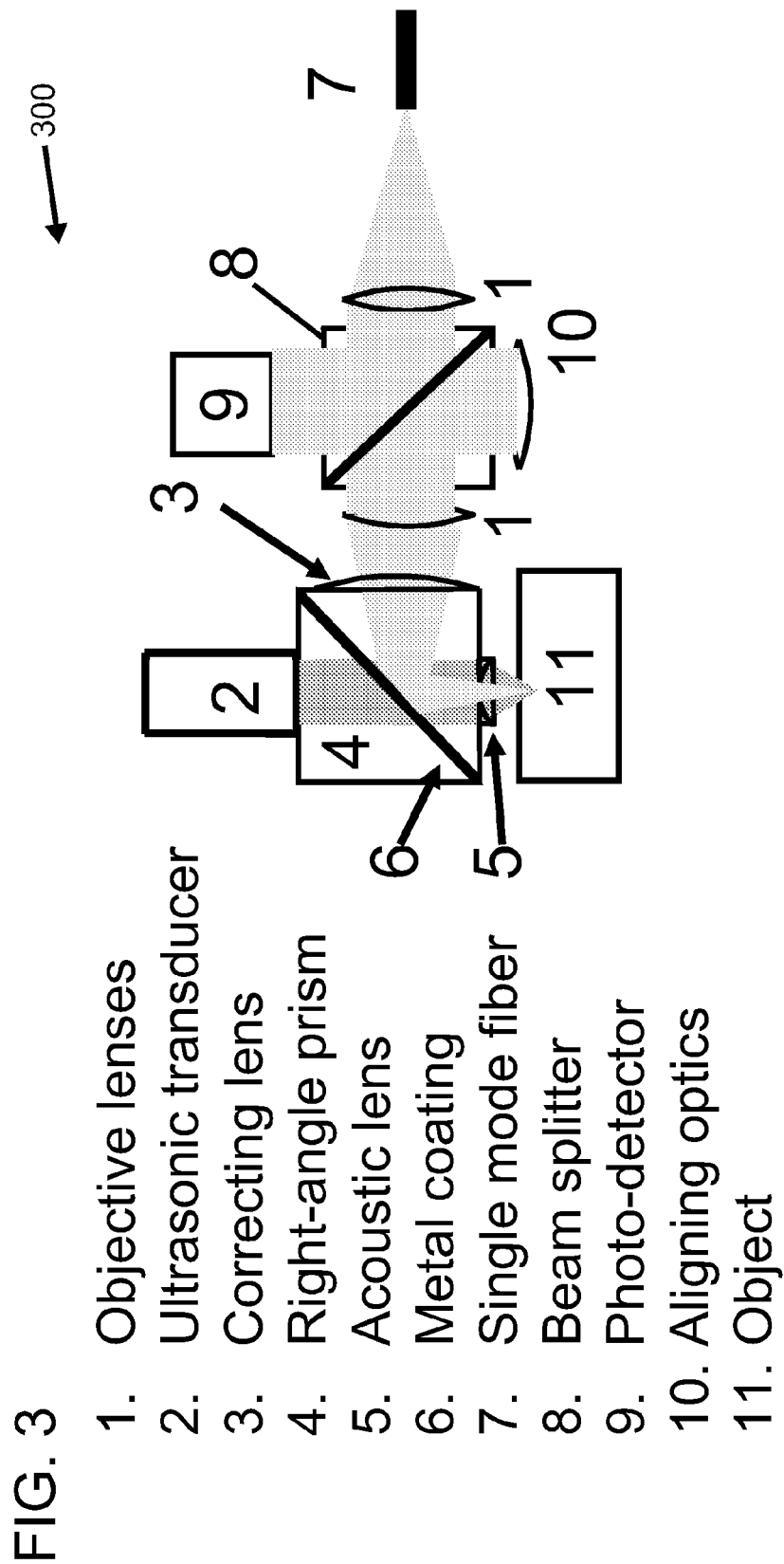
FIG. 3 is a diagram of a photoacoustic sensor that may be used with the imaging system shown in FIG. 2.

FIG. 3 is a diagram of a focusing assembly 300 of imaging system 200 (shown in FIG. 2). A custom-made cubic beam splitter or right-angle prism 4 with a sub-micron reflective aluminum coating layer 6 sandwiched between the two prisms is used to couple the optical and ultrasonic radiations. A pair of optical objective lenses 1 focuses the laser light from the single-mode optical fiber onto the region of interest inside the object, where metal coating 6 is used to reflect the optical beam. A sampling beam splitter 8 is placed between the objective lenses 1 to monitor the laser output power with a photo-detector 9 and to view the object surface for alignment with an eyepiece or aligning optics 10. Ultrasonic radiation emitted by the object 11 passes through an acoustic lens 5, the aluminum optical reflector, and reaches an ultrasonic transducer 2.

Figure 4:
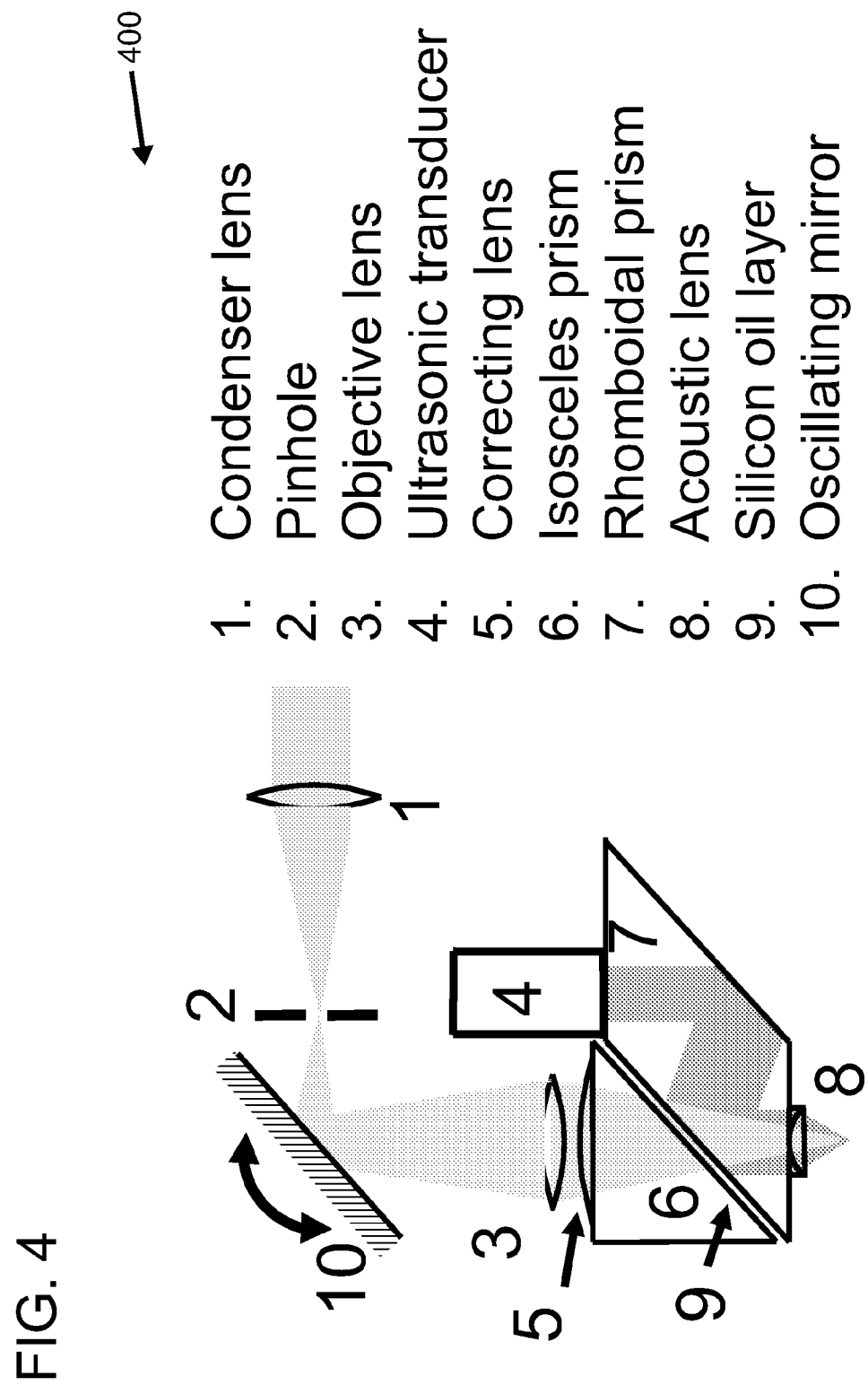
FIG. 4 is a diagram of an alternative photoacoustic sensor that may be used with the imaging system shown in FIG. 2.

FIG. 4 is a diagram of a focusing assembly 400 of imaging system 200 (shown in FIG. 2). A laser pulse from a pulse laser is focused by a condenser lens 1 on a diaphragm 2 for spatial filtering. The light coming out of the spatial filter 2 is reflected by an oscillating mirror 10, which performs fast optical scanning within the wider focal area of an ultrasonic transducer 4. The laser beam is focused into an object by a microscope objective lens 3 through a beam splitting element 6, 7, 9 and an acoustic lens 8. A thin plano-convex optical lens 5 is placed on top of the beam splitting element 6, 7, 9 to compensate for the aberrations introduced by the prisms 6 and 7 and the acoustic lens 8. The beam splitting element 6, 7, 9 consists of an isosceles triangular prism 6 with an apex angle of 52.5° and a rhomboidal 52.5° prism 7. Prisms 6 and 7 are adjoined along the diagonal surfaces but are separated by a thin layer of refractive-index-matching, low-acoustic-impedance, and nonvolatile liquid, such as a low-molecular-weight silicone oil 9. The photoacoustic signal emitted by the object is transformed by the acoustic lens 8 into a plane elastic wave in rhomboidal prism 7. Ultrasonic reflection from the boundary of silicone oil 9 converts at least 98% of the energy of the incident longitudinal wave into that of a shear wave, which is transformed back into a longitudinal wave on the free surface of rhomboidal prism 7 and then detected by high-frequency direct-contact ultrasonic transducer 4. Because the acoustic focus is generally several times wider than the optical focus, taking advantage of fast optical scanning in this embodiment may significantly decrease the image acquisition time.

Figure 5:
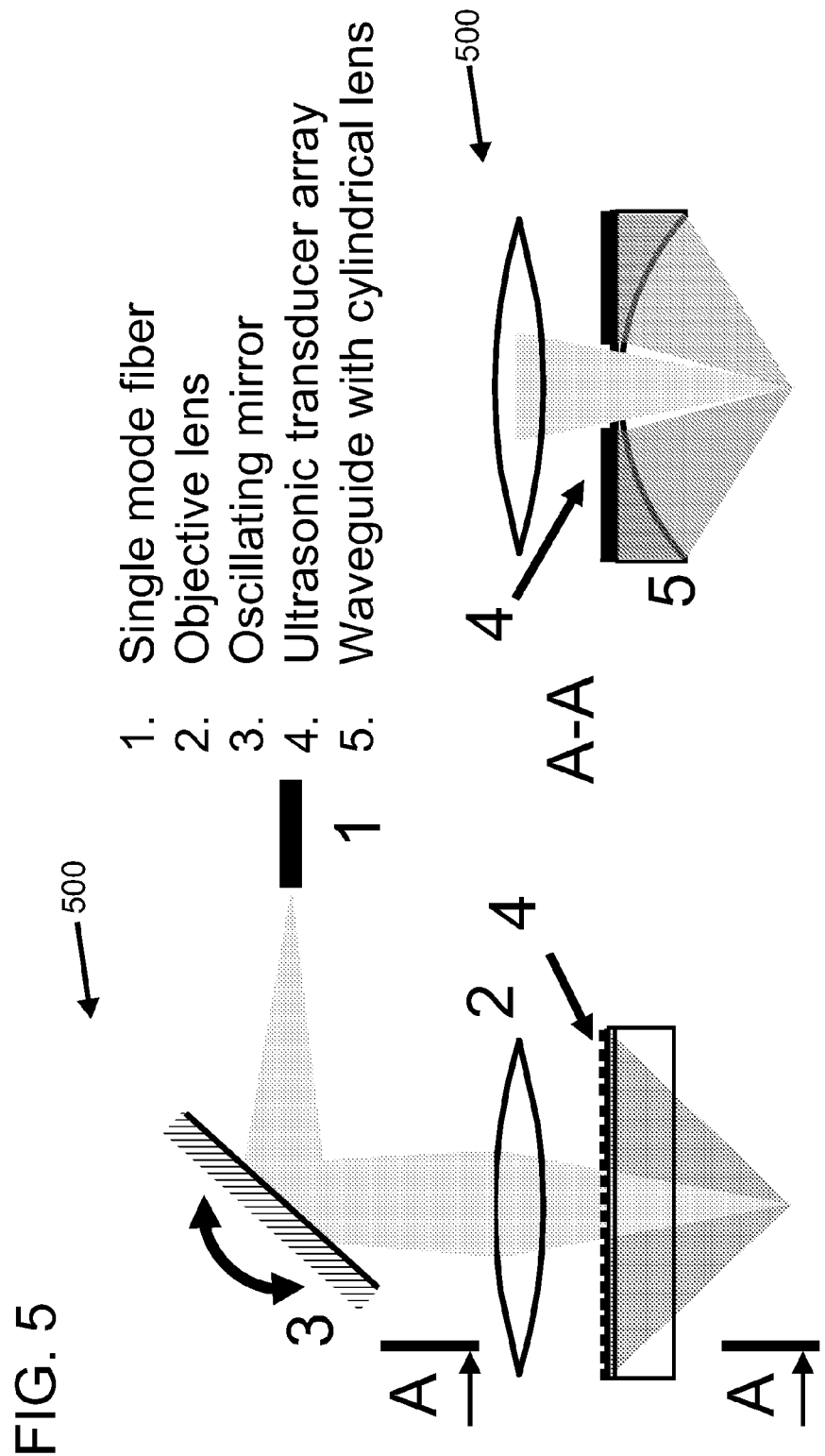
FIG. 5 is a diagram of a second alternative photoacoustic sensor that may be used with the imaging system shown in FIG. 2.

FIG. 5 is a diagram of a focusing assembly 500 of imaging system 200 (shown in FIG. 2). An optical objective lens 2 focuses the output aperture of a single-mode optical fiber 1 into the object through the optically clear slit window in a one-dimensional ultrasonic array transducer 4 placed on an optically transparent substrate 5. Substrate 5 serves as a waveguide for acoustic waves and may have a cylindrical focus acoustic lens on its outer surface. The light coming out of the spatial filter is reflected by an oscillating mirror 3, which performs fast optical scanning. Ultrasonic radiation emitted by the object is collected by ultrasonic transducer array 4. A multiple-element piezoelectric transducer array may accelerate the image acquisition time in one dimension owing to the electronic focusing of the transducer array. The acoustic focus provided by assembly 500 follows the focal position of the laser beam without mechanically scanning the ultrasonic transducer over the object. Three-dimensional images may be acquired by mechanically translating the focusing assembly perpendicularly to the slit.

Figure 6:
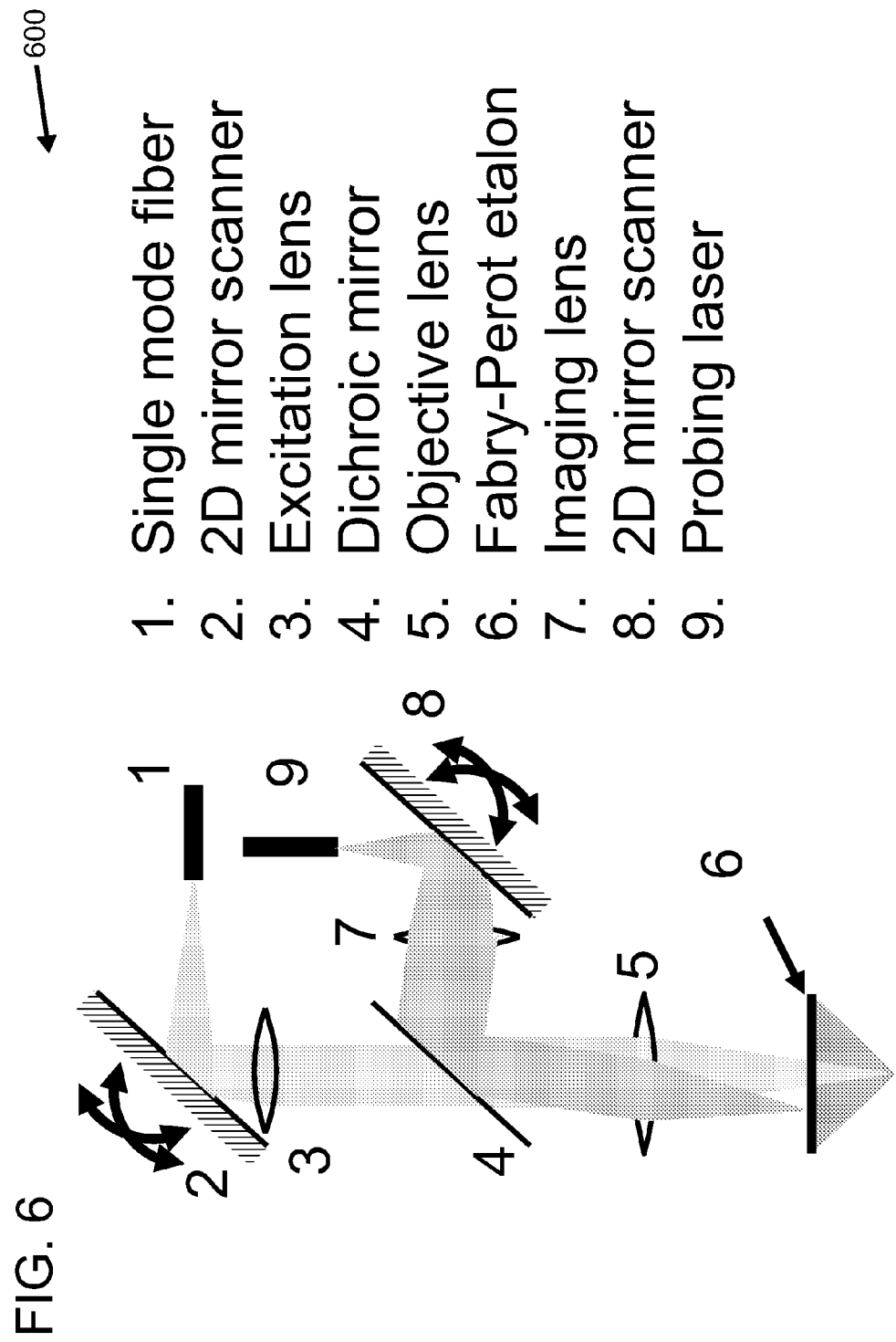
FIG. 6 is a schematic diagram of a third alternative photoacoustic sensor that may be used with the imaging system shown in FIG. 2.

FIG. 6 is a diagram of a focusing assembly 600 of imaging system 200 (shown in FIG. 2). The light output from a single-mode optical fiber 1 is reflected by a mirror scanner 2, collimated by an optical objective or excitation lens 3, passed through a dichroic mirror 4, and then focused by another objective lens 5 on a region of interest through a Fabry-Perot etalon 6, which is acoustically coupled to the object. Mirror scanner 2 performs rapid 2D raster scanning of the object by sweeping the excitation laser beam. The photoacoustic wave from the object causes a transient strain distribution in Fabry-Perot etalon 6, which shifts its resonance wavelengths. Another laser (probing laser) 9 working at a different optical wavelength scans over Fabry-Perot etalon 6 through a second mirror scanner 8, a second objective lens 7, and dichroic mirror 4 to read the strain distribution in Fabry-Perot etalon 6. The strain is then converted into the photoacoustic pressure distribution. In the exemplary embodiment, no mechanical scanning is necessary to form a 3D image of the object.

Figure 7:
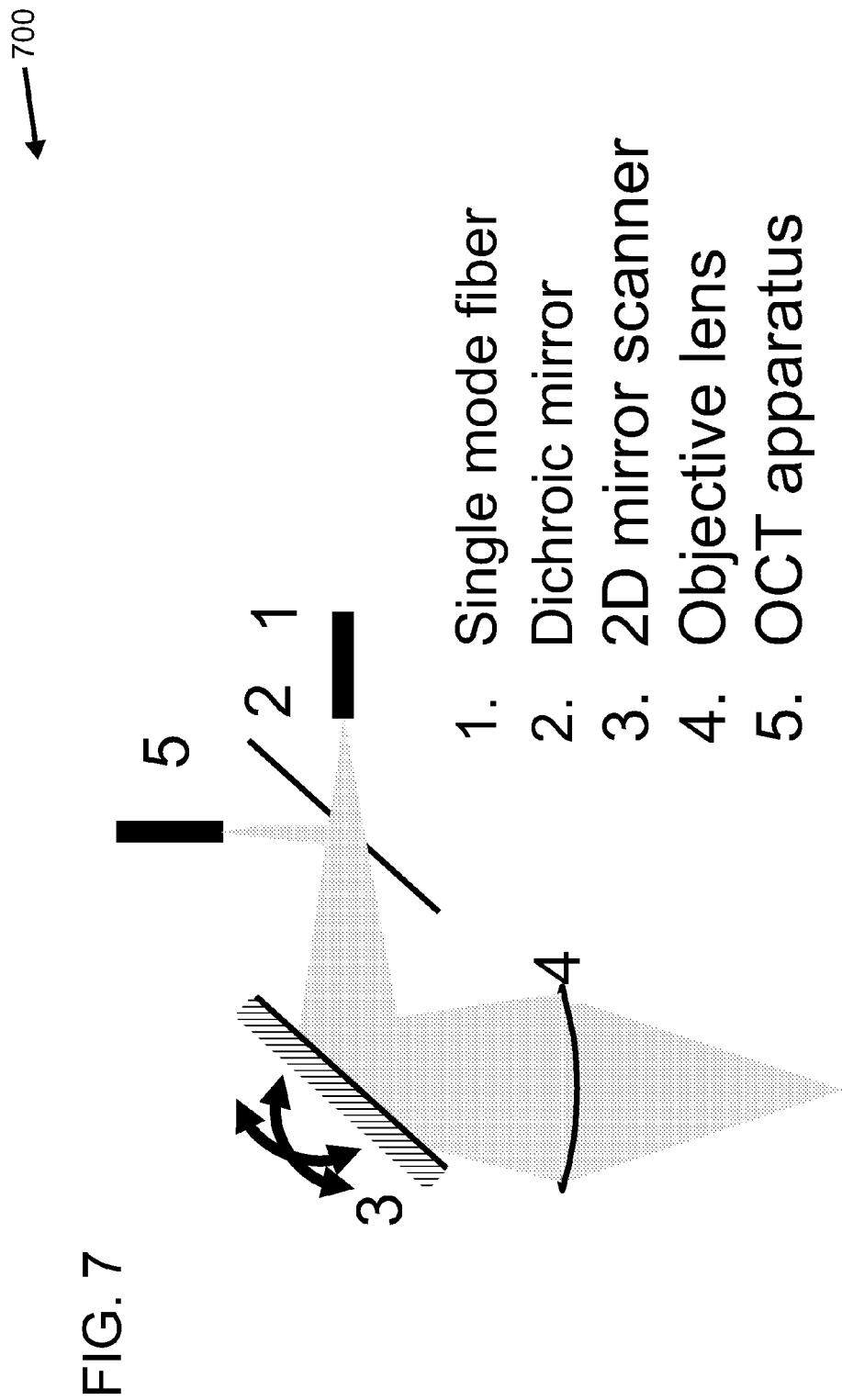
FIG. 7 is a schematic diagram of a fourth alternative photoacoustic sensor that may be used with the imaging system shown in FIG. 2.

FIG. 7 is a diagram of a focusing assembly 700 of imaging system 200 (shown in FIG. 2). An optical objective lens 4 focuses the output aperture of a single-mode optical fiber 1 into a region of interest in an object to excite photoacoustic waves. A 2D mirror scanner 3 is introduced in the optical path to perform 2D scanning of the object. A phase-sensitive optical coherence tomography (OCT) system 5 working at a different optical wavelength is focused on the same region of interest by the optical objective lens 4 and 2D mirror scanner 3. The two light beams of different wavelengths are coupled by a dichroic mirror 2. The phase-sensitive OCT system measures, within the optical focal spot inside the object, the photothermal effect due to absorption of the laser pulse. The photothermal effect in the object is measured before pressure waves propagate to the surface of the object. In the exemplary embodiment, focusing assembly 700 forms a 3D image without translating the objective lens and does not require direct contact with the object. Correspondingly, it may be potentially very fast and may be used where non-contact imaging is preferred.

Figure 8:
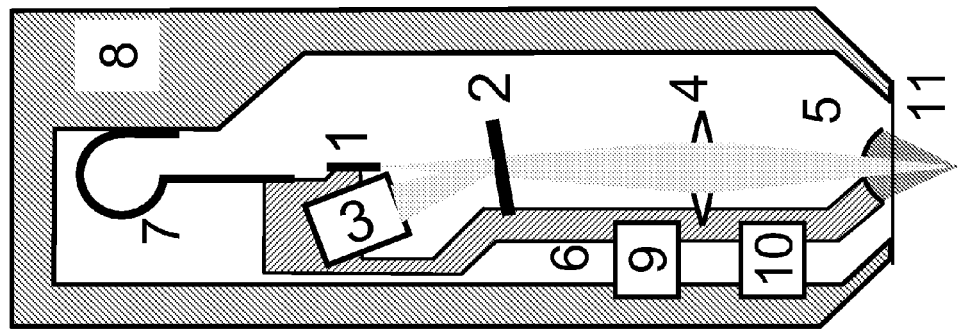
FIG. 8 is a diagram of a fifth alternative photoacoustic sensor that may be used with the imaging system shown in FIG. 2.

FIG. 8 is a diagram of an alternative embodiment of the focusing assembly 800 suitable for hand-held operation. An optical objective lens 4 images the aperture of a single-mode optical fiber 1 onto the region of interest in the object through an optically clear window in a spherically focused ultrasonic transducer 5. A sampling beam splitter 2 reflects a small portion of the incident light to monitor the laser output power with a photo-detector 3. The ultrasonic radiation emitted by the object is received by the ultrasonic transducer 5. The photoacoustic assembly is mounted on a pendulum 6, which is attached to a frame 8 through a flexible mount, such as a flat spring 7. The frame is water-tight and contains optically transparent acoustic coupling fluid, such as water, for light delivery and acoustic coupling. Moved by an actuator 9, pendulum 6 may perform sector scanning of the object rapidly. A position sensor 10 monitors the position of the optical focus and is used to synchronize the pulse laser so that image distortion due to varying scanning velocity is minimized.

Figure 9:
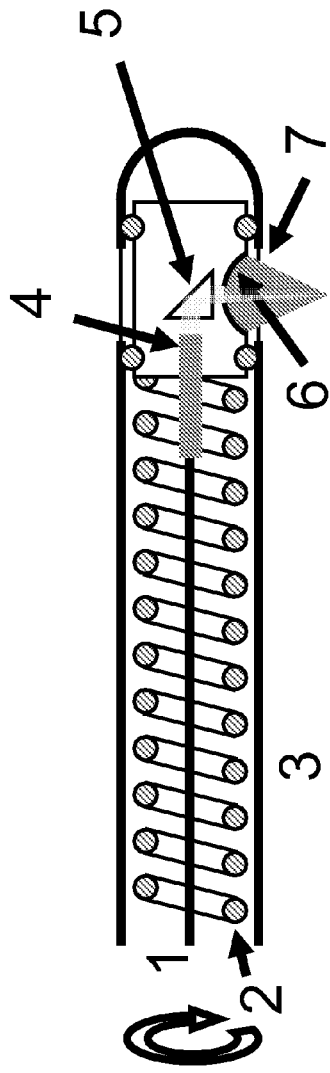
FIG. 9 is a schematic diagram of a sixth alternative photoacoustic sensor that may be used with the imaging system shown in FIG. 2.

FIG. 9 is a diagram of another alternative embodiment of a focusing assembly 900 suitable for applications inside body cavities such as inter-vascular imaging. A laser pulse delivered by a single-mode fiber 1 is focused on the region of interest in the object by an optical lens assembly 4 through an optically clear window in a spherically focused ultrasonic transducer 6. Ultrasonic transducer 6 together with a right-angled prism 5 is connected to a flexible shaft 2 located inside a catheter 3. Optically and acoustically transparent circular window 7 allows the optical beam and ultrasonic radiation to pass freely to and from the object. Photoacoustic images are formed by rotating the shaft 2 with respect to the axis of the catheter and axially translating the catheter.

Figure 10:
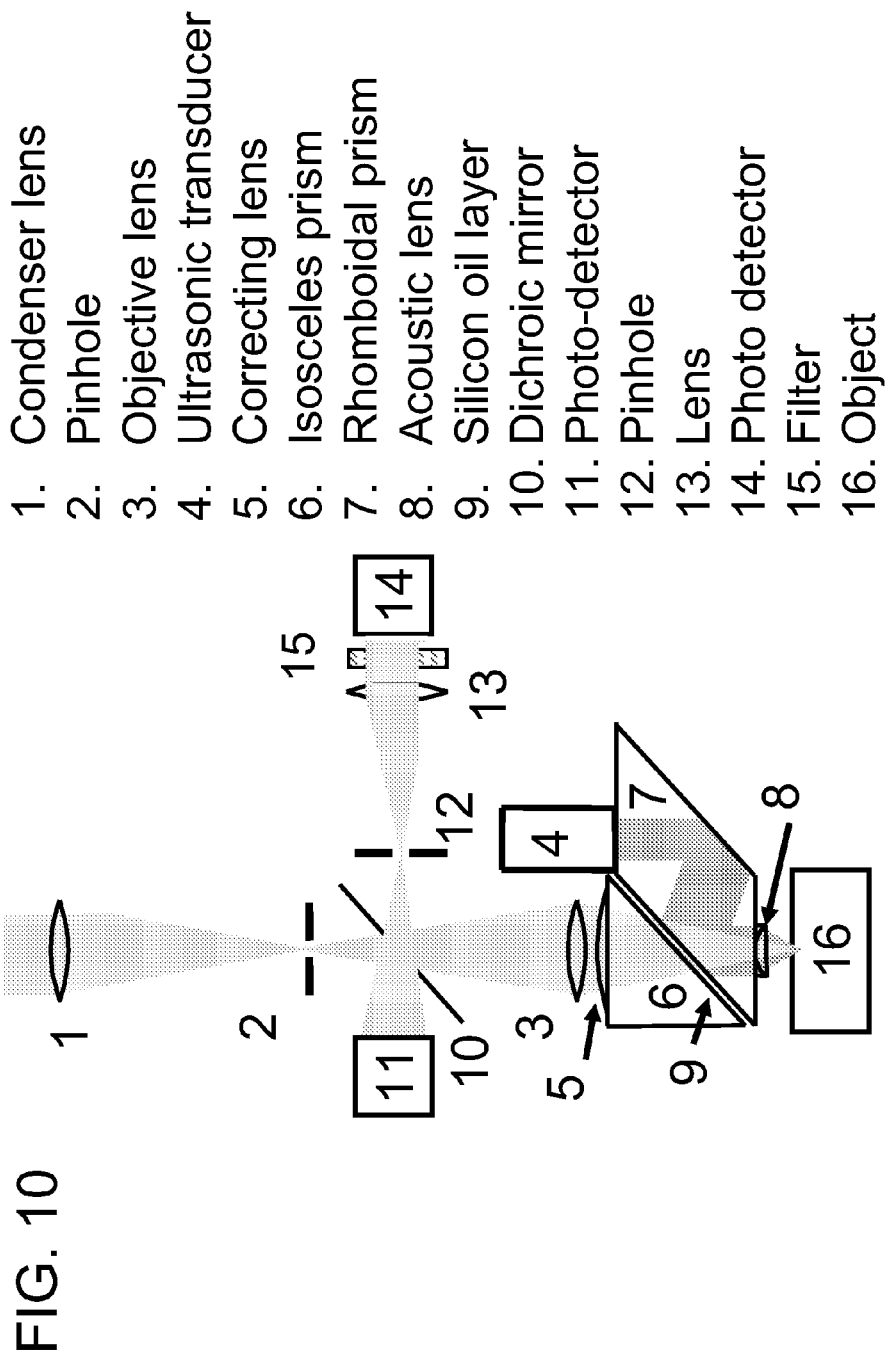
FIG. 10 is a schematic diagram of a seventh alternative photoacoustic sensor that may be used with the imaging system shown in FIG. 2.

FIG. 10 is a block diagram of another alternative embodiment of a focusing assembly 1000 which uses the confocal photoacoustic microscopy method simultaneously with optical confocal microscopy. The light coming out of the pulsed laser is focused by a condenser lens 1 on a diaphragm (pinhole) 2 for spatial filtering. A dichroic beam splitter or mirror 10 is used to monitor the laser output power with a photo-detector 11 and to form an optical fluorescence confocal image of the object. The optical fluorescence confocal imaging portion consists of a pinhole, or diaphragm, 12, a focusing system or lens 13, a low pass optical filter 15, and a photo-detector (such as a photomultiplier) 14. The light coming out of the spatial filter is focused by a microscope objective lens 3 on the object through a beam splitting element. The beam splitting element consists of an isosceles triangular prism 6 with an apex angle of 52.5° and a rhomboidal 52.5° prism 7. Prisms 6 and 7 are adjoined along the diagonal surfaces with a gap in between 9. Gap 9 is filled with refractive-index-matching, low-acoustic-impedance, nonvolatile liquid. A correction lens 5 is placed on top of the beam splitting element to compensate for aberrations introduced by the prisms and the acoustic lens. The photoacoustic signal emitted by the object is transformed by an acoustic lens 8 into a plane elastic wave in rhomboidal prism 7. Ultrasonic reflection from the boundary of the prism converts the incident longitudinal elastic wave into a shear wave. The shear wave propagates toward the free surface of the rhomboidal prism, where it is transformed back into a longitudinal wave and detected by a high-frequency direct-contact ultrasonic transducer 4 for image formation and spectral measurements of the target.

The fusion of the optical confocal microscopy and photoacoustic microscopy provides complementary information about the object. One feature is the quantitative measurement of the optical absorption spectrum of the object by simultaneously using the fluorescence signal from the optical confocal microscope and the photoacoustic signal from the photoacoustic microscope. The quantitative measurement of the optical absorption spectrum of the object requires knowledge of the spectral variation of the excitation optical fluence at the focus, which may be measured using the fluorescent signals as illustrated below.

In the exemplary embodiment, two excitation optical wavelengths are used. If a fluorescence dye is present, the detected fluorescence signal $V_f(\lambda_{xi}, \lambda_m)$ at the i-th excitation wavelength $\lambda_{xi}$ and the emission wavelength $\lambda_m$ is a product of the unknown local excitation optical fluence, the concentration of dye C, the known molar optical absorption coefficient of the dye $\epsilon_{af}(\lambda_{xi})$, the quantum yield of the dye Q, and the fluorescence detection sensitivity $S_f(\lambda_m)$. For i=1 and 2, the following ratio in Equation (1) is present:

$$\frac{V_f(\lambda_{x1}, \lambda_m)}{V_f(\lambda_{x2}, \lambda_m)} = \frac{\epsilon_{af}(\lambda_{x1}) F(\lambda_{x1})}{\epsilon_{af}(\lambda_{x2}) F(\lambda_{x2})}. \quad (1)$$

Therefore, the local excitation optical fluence ratio may be recovered as in Equation (2):

$$\frac{F(\lambda_{x1})}{F(\lambda_{x2})} = \frac{V_f(\lambda_{x1}, \lambda_m)}{V_f(\lambda_{x2}, \lambda_m)} \bigg/ \frac{\epsilon_{af}(\lambda_{x1})}{\epsilon_{af}(\lambda_{x2})}. \quad (2)$$

Similarly, the detected photoacoustic signal $V_{pa}(\lambda_{xi})$ is a product of the local excitation optical fluence $F(\lambda_{xi})$, the optical absorption coefficient of dominantly absorbing hemoglobin $\mu_{ah}(\lambda_{xi})$ and the acoustic detection sensitivity Sa. Assuming that the hemoglobin absorbs much more than the fluorescent dye, the following ratio in Equation (3) is developed:

$$\frac{V_{pa}(\lambda_{x1}, \lambda_m)}{V_{pa}(\lambda_{x2}, \lambda_m)} = \frac{\mu_{ah}(\lambda_{x1}) F(\lambda_{x1})}{\mu_{ah}(\lambda_{x2}) F(\lambda_{x2})}. \quad (3)$$

From the above two equations, the ratio of the hemoglobin absorption coefficient may be recovered as in Equation (4):

$$\frac{\mu_{ah}(\lambda_{x1})}{\mu_{ah}(\lambda_{x2})} = \frac{V_{pa}(\lambda_{x1}, \lambda_m)}{V_{pa}(\lambda_{x2}, \lambda_m)} \frac{V_f(\lambda_{x2}, \lambda_m)}{V_f(\lambda_{x1}, \lambda_m)} \frac{\epsilon_{af}(\lambda_{x1})}{\epsilon_{af}(\lambda_{x2})}. \quad (4)$$

This ratio may be used to quantify the oxygen saturation of hemoglobin and the relative total concentration of hemoglobin. Of course, this example merely illustrates the principle, which may be extended to the measurement of other optical absorbers using two or more excitation optical wavelengths.

The presently described embodiments may be used to estimate oxygen metabolism in tissues and organs, by combining measurements of blood flow and oxygenation into and out of regions of interest. Oxygen metabolic rate (MRO2) is the amount of oxygen consumed in a given tissue region per unit time per 100 grams (g) of tissue or of the organ of interest. Since in typical physiological conditions, hemoglobin is the dominant carrier of oxygen, the key measure of blood oxygenation is oxygen saturation of hemoglobin (SO2), as follows in Equation (5):

$$MRO_2 \propto (SO_{2,in} - SO_{2,out}) \cdot C_{Hb} \cdot A_{in} \cdot \bar{v}_{in}. \quad (5)$$

Here, $A_{in}$ is the area of the incoming vessel, $\bar{v}_{in}$ is the mean flow velocity of blood in the incoming vessel, and $C_{Hb}$ is the total concentration of hemoglobin. While $A_{in}$ and $\bar{v}_{in}$ may be estimated using ultrasound imaging, SO2 and relative $C_{Hb}$ may be estimated from multi-wavelength photoacoustic methods.

Exemplary advantages of photoacoustic microscopy over traditional optical and ultrasonic imaging include the detection of endogenous optical absorption contrast at ultrasonic resolution. In photoacoustic microscopy, a pulsed laser beam is focused into the biological tissue to produce emission of ultrasonic waves due to the photoacoustic effect. The short-wavelength pulsed ultrasonic waves are then detected with a focused ultrasonic transducer to form high-resolution tomographic images. Among the existing photoacoustic imaging technologies, the spatial resolutions depend almost solely on the ultrasonic parameters including the center frequency, bandwidth, and numerical aperture (NA). For example, using dark-field confocal PAM, a lateral resolution of approximately 50 µm has been achieved with a center frequency of approximately 50 megahertz (MHz) and an NA of approximately 0.44. This resolution from prior systems is inadequate to resolve smaller structures such as capillaries between approximately 3 µm and approximately 7 µm in diameter with endogenous optical absorption contrast. Aspects of the invention provide improved spatial resolution.

If such an improvement is achieved by increasing the ultrasonic focusing capability, an approximately 5-µm lateral resolution requires an ultrasonic center frequency greater than 300 MHz. At such a high frequency, unfortunately, the ultrasonic attenuation, which is approximately 400 µm$^{-1}$ in water and 100 µm$^{-1}$ in tissue, limits the penetration depth to approximately 100 µm. An alternative is to use fine optical focusing to provide the lateral resolution while ultrasonic temporal detection provides axial resolution. Such an alternative, called OR-PAM, is primarily sensitive to optical absorption contrast, whereas conventional reflection-mode optical confocal microscopy is dominantly sensitive to scattering or fluorescence.

Figure 11:
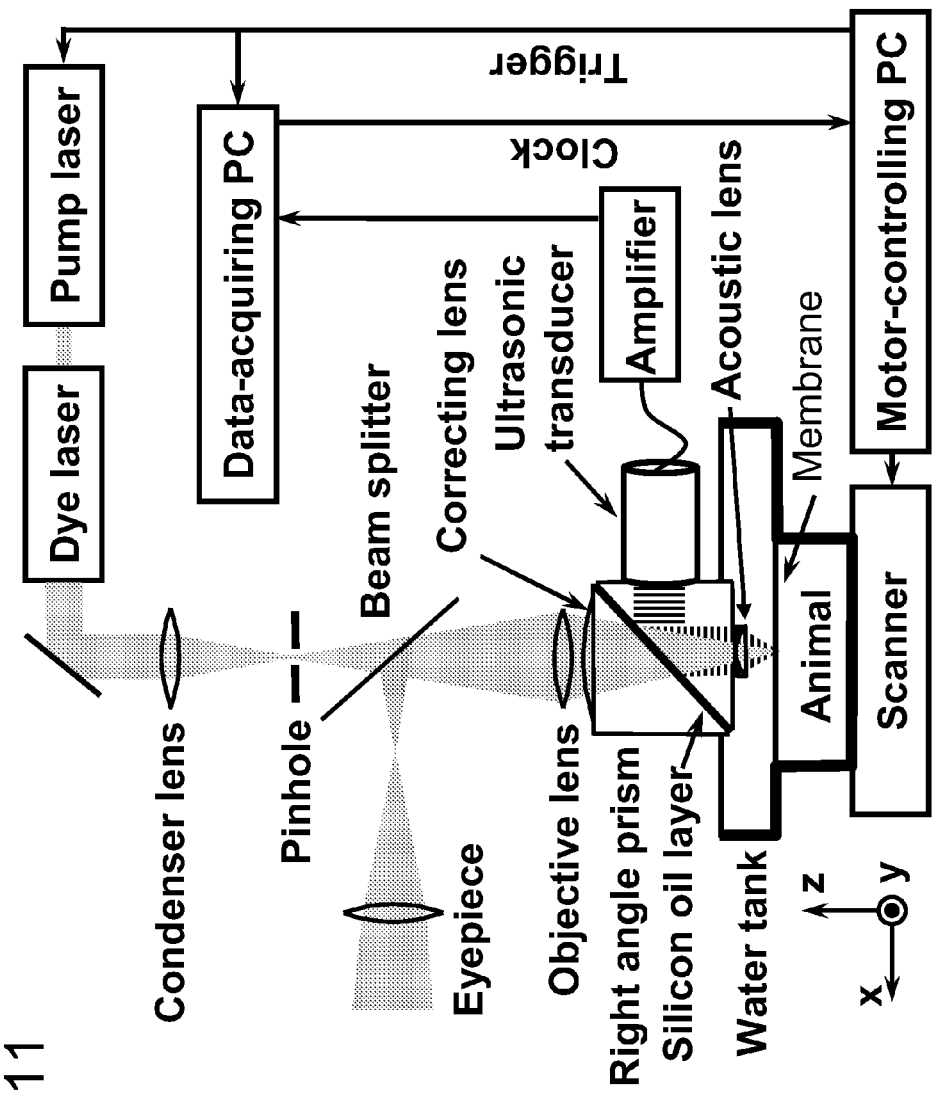
FIG. 11 is a schematic diagram of an eighth photoacoustic sensor that may be used with the imaging system shown in FIG. 2.

FIG. 11 is a schematic of another exemplary embodiment of the OR-PAM imaging system. In this embodiment, the system employs nearly diffraction limited optical focusing with bright field optical illumination to achieve µm-level lateral resolution. A dye laser, such as a CBR-D laser commercially available from Sirah, pumped by a Nd:YLF laser is used as the irradiation source. The laser pulse duration is approximately 5 ns and the pulse repetition rate, controlled by an external trigger, is as high as 2 kHz. The light from the dye laser is attenuated by one thousand times, passed through a spatial filter, such as a 25 µm pinhole, commercially available as P250S from Thorlabs, and then focused by a microscope objective lens, such as a RMS4X lens available from Thorlabs and including a NA of approximately 0.1, a focal length of approximately 45 mm, and a working distance of approximately 22 mm. The distance between the pinhole and the objective lens is approximately 400 mm. The input aperture of the microscope objective is approximately 0.8 times the diameter of the Airy disk of the spatial filter. As a result, the diffraction-limited focus of the objective in water is approximately 3.7 µm in diameter and approximately 200 µm in focal zone. The laser pulse energy after the objective lens measures approximately 100 nJ. An optional beam splitter is located between the pinhole and the objective lens to facilitate focus adjustment and system alignment. Two right-angled prisms, the NT32-545 prism available from Edmund Optics, for example, form a cube with a gap of approximately 0.1 mm between the hypotenuses. The gap is filled with silicone oil. As described above, the silicone oil and the glass have a good optical refractive index match but a large acoustic impedance mismatch. As a result, this silicone oil layer is optically transparent but acoustically reflecting. An ultrasonic transducer, such as a V2012-BC transducer available from Panametrics-NDT, with a center frequency of 75 MHz, a bandwidth of 80%, and an active-element diameter of 6.35 mm, is attached to a cathetus of the bottom prism as shown in FIG. 11. A plano-concave lens with an approximately 5.2 mm radius of curvature and an approximately 6.35 mm aperture is attached to the bottom of the cube to function as an acoustic lens, which has an NA of approximately 0.46 in water and a focal diameter of approximately 27 µm. Of course, this lens also functions as a negative optical lens, which is compensated for by a correcting positive optical lens placed on top of the cube.

The photoacoustic signal detected by the ultrasonic transducer is amplified by approximately 48 dB using, for example, two ZFL 500LN amplifiers commercially available from Mini-Circuits, then digitized by a 14-bit digital acquisition board using, for example, a CompuScope 12400 from Gage Applied Sciences. A raster scanning is controlled by a separate PC, which triggers both the data-acquisition PC and the pump laser. The trigger signal is synchronized with the clock-out signal from the digital acquisition board.

An acoustic lens is immersed in water inside a heated container. A window is opened at the bottom of the container and sealed with an ultrasonically and optically transparent 25-µm thick polyethylene membrane. The animal is placed under the water tank with the region of interest (ROI) exposed below the window. Ultrasonic gel, such as Clear Image, available from SonoTech, is applied to the ROI for acoustic coupling. For simplicity, the raster scanning is implemented by translating the water tank and the animal together along the horizontal (x-y) plane. One-dimensional (1D) photoacoustic signal (A-line) at each horizontal location is recorded for 1 µs at a sampling rate of 200 MS/s. A volumetric photoacoustic image is formed by combining the time-resolved photoacoustic signals and may be viewed in direct volumetric rendering, cross-sectional (B-scan) images, or maximum amplitude projection (MAP) images.

FIGS. 12A-12C are images representing a lateral resolution measurement by the imaging system. FIG. 12A is a MAP image of an Air Force resolution test target, FIG. 12B is a magnified image of the region within the dashed box of FIG. 12A, and FIG. 12C is a MAP image of a 6-µm-diameter carbon fiber. The lateral resolution of the OR-PAM system was experimentally measured by imaging an Air Force resolution test target immersed in clear liquid. Images were acquired at the optical wavelength of approximately 590 nm and no signal averaging was performed during data acquisition. In FIGS. 12A and 12B, the highlighted well-resolved bars, shown as group 6, element 5, have gaps of approximately 4.9 µm, a spatial frequency of approximately 102 mm$^{-1}$, and a modulation transfer function value of 0.65. Other pairs of spatial frequency and modulation transfer function values include, for example, a 64 mm$^{-1}$ spatial frequency with a 0.95 modulation transfer function value, and an 80 mm$^{-1}$ spatial frequency with a 0.8 modulation transfer function value. Nonlinearly fitting of the modulation transfer function yields a lateral resolution of approximately 5 µm, which is 30% greater than the diffraction limit of 3.7 µm. As an illustration of the lateral resolution, an MAP image of a 6-µm-diameter carbon fiber immersed in water is shown in FIG. 12C. The mean full-width-at-half-maximum (FWHM) value of the imaged fiber is approximately 9.8 µm, which is 3.8 µm wider than the fiber diameter and hence in agreement with the ~5 µm resolution. The axial resolution was estimated to be approximately 15 µm based on the measured transducer bandwidth, approximately 100 MHz in receiving-only mode, and the speed of sound in tissue, approximately 1.5 mm/µs. In tissue, both the lateral and the axial resolutions deteriorate with imaging depth because of optical scattering and frequency-dependent acoustic attenuation, respectively.

Figures 13A, 13B:
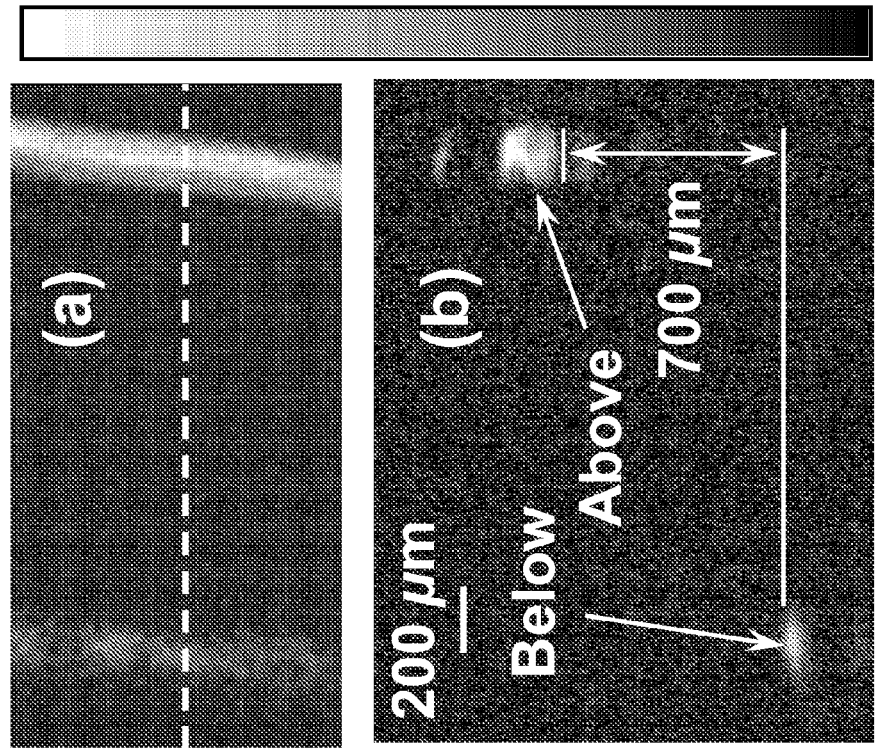
FIGS. 13A and 13B are images representing a measurement of the imaging depth by the imaging system.

FIGS. 13A and 13B are images representing a measurement of the imaging depth by the imaging system. FIG. 13A is a MAP image of two horse hairs placed above and below a piece of rat skin acquired with the OR-PAM system. FIG. 13B is a B-scan image at the location marked by the dashed line in FIG. 13A. The imaging depth of this system was measured by imaging two horse hairs with a diameter of approximately 200 µm placed above and below a piece of freshly harvested rat scalp. A photoacoustic image was acquired with 32 times signal averaging at the optical wavelength of 630 nm. Both hairs are clearly visible, where the bottom hair shows a weaker photoacoustic signal because of both optical and acoustic attenuation in the skin. The B-scan image shows that the bottom hair is 700 µm deep in the tissue. Therefore, the maximum imaging depth is at least 700 µm.

The microvessels in the ear of a nude mouse were imaged in vivo by this OR-PAM at the optical wavelength of 570 nm. Nude mouse ears having a thickness of approximately 300 µm have well-developed vasculature and have been widely used to study tumor angiogenesis and other microvascular diseases. During image acquisition, the animal was kept motionless using a breathing anesthesia system and was kept warm using an infrared lamp. Unlike studies published elsewhere, no optical clearing agent was applied to the skin surface. An area of 1 mm$^2$ was scanned with a step size of approximately 1.25 µm. For each pixel, 16 (i.e., 4 by 4) neighboring A-lines were averaged to increase the signal-to-noise ratio (SNR). The scanning time for a complete volumetric dataset was approximately 18 minutes. After data acquisition, the animal recovered naturally without observable laser damage.

Figure 14A:
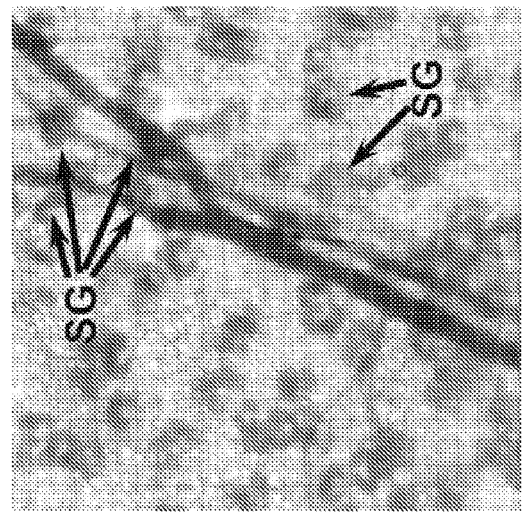
FIGS. 14A and 14B are photoacoustic images of a microvasculature by the imaging system.
Figure 14B:
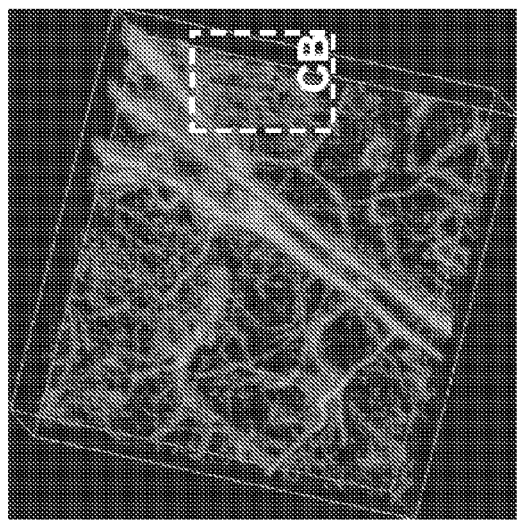
Figure 14C:
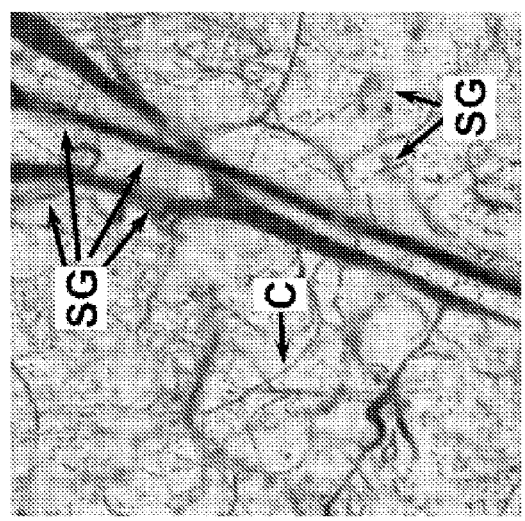
FIG. 14C is a photograph of the microvasculature of FIGS. 14A and 14B, taken from a transmission microscope.

FIGS. 14A and 14B are photoacoustic images of a microvasculature by the imaging system. FIG. 14C is a photograph of the microvasculature of FIGS. 14A and 14B, taken from a transmission microscope. More specifically, FIG. 14A is an in vivo photoacoustic image of microvasculature in a nude mouse ear, FIG. 14B is a 3D visualization of the volumetric photoacoustic data with pseudocolor, and FIG. 14C is a photograph taken with trans-illumination optical microscopy. In FIGS. 14A-14C, the area denoted as C is a capillary, the area denoted as CB is a capillary bed, and the area denoted as SG is a sebaceous gland. The photoacoustic image of the microvasculature (FIGS. 14A and 14B) agrees with the photograph (FIG. 14C) taken from a transmission microscope with a 4× magnification. However, capillaries are imaged by only the OR-PAM system described above. The mean ratio of the photoacoustic amplitudes between the blood vessels and the background is 20:1, which demonstrates a high endogenous optical-absorption-based imaging contrast. Some vessels, e.g. the vessel labeled with C in FIG. 14A, only occupy a single pixel, which presumably indicates a capillary with a diameter of approximately 5 μm. A volumetric rendering of the photoacoustic data (FIG. 14B) shows the three-dimensional connectivity of the blood vessels. Parallel arteriole-venule pairs and their branching are clearly observed. The diameter and the morphological pattern of the vessel within the dashed-box in both FIGS. 14A and 14B suggest that these microvessels belong to a capillary bed. Therefore, OR-PAM, as described above, is able to image capillaries in vivo with endogenous optical absorption contrast due to hemoglobin. In addition, sebaceous glands may also be imaged at the same time.

FIGS. 15A and 15B are MAP images acquired before and after a high-intensity laser treatment. FIG. 15A is an in vivo photoacoustic image of laser-induced vessel destruction in a Swiss Webster mouse ear before a laser treatment. FIG. 15B is an in vivo photoacoustic image after the laser treatment. In FIGS. 15A and 15B, the area denoted as T is the laser treated area, the area denoted as W is widened blood vessels, and the area denoted as H is a possible hemorrhage. To further demonstrate the potential of OR-PAM, the high-intensity laser destruction of microvessels in the ear of a Swiss Webster mouse were imaged. This type of destruction is clinically used to remove port wine stains in humans. FIGS. 15A and 15B show the MAP images acquired before and after the high-intensity laser treatment. After the healthy vasculature was imaged by the OR-PAM system (shown in FIG. 15A), the center region measuring approximately 0.25×0.25 mm$^2$ was treated by high-intensity laser pulses having a peak optical fluence of approximately 10 J/cm$^2$ scanned with the step size of approximately 1.25 μm. For the high-intensity illumination, the attenuator and the pin hole were removed from the light path. A second image (shown in FIG. 15B) was acquired 15 minutes after the laser treatment. Disruption of the vessels within the treated region was clearly observed in the dashed box. Further, the destruction of the blood vessels dilated several neighboring vessels and produced possibly hemorrhage.

FIG. 16A is an in vivo photoacoustic image of a capillary bed in a mouse ear, captured using the OR-PAM imaging system with a focusing depth of approximately 50 μm. FIG. 16B is an in vivo photoacoustic image of multiple levels of blood vessel bifurcations in a mouse ear, captured using the OR-PAM imaging systems with a focusing depths of approximately 150 μm.

The embodiments described herein use (1) optical focusing to achieve high lateral resolution, (2) time-resolved detection of laser-induced pressure waves to obtain high axial resolution, and/or (3) confocal arrangement between the optical excitation and ultrasonic receiving foci to achieve high sensitivity. In alternative embodiments, the focused ultrasonic receiving may be replaced with optical sensing of the photo-thermal effect directly inside the object. Three-dimensional images of the distribution of optical contrast within a sampling volume are acquired.

In an existing system, an intensity-modulated continuous-wave beam of radiation is combined with the detection of the magnitude of the photoacoustic signal. In the embodiments described herein, short pulsed excitation is combined with time-resolved detection of the photoacoustic signal, which has the advantage of time-of-flight based axial resolution. Therefore, the presently described embodiments provide, for example, (a) enhanced axial resolution, (b) 3D imaging of optical contrast from a 2D raster scan, and (c) minimal image artifacts due to the interference of photoacoustic waves from various targets within the light illumination volume, in contrast to the existing system.

Another existing system uses focused light to produce thermal expansion and uses optical detection, based on the thermal lens effect, or an ultrasonic detector to monitor the resulting pressure/density transients. Such a system lacks axial resolution. In addition, the lateral resolution of such a system is determined by the detector rather then the excitation optics. Utilization of the thermal lens effect in such a system requires transmission illumination in an optically clear medium, which limits the applications of the technology. Moreover, in using an unfocused ultrasonic transducer and an unfocused ultrasonic detector, the excitation beam has a large separation, which affects the detection sensitivity. The frequency mismatch between the central frequency of the photoacoustic waves (>100 MHz) and the central frequency of the ultrasonic transducer (<10 MHz) also limits the SNR of such a system.

Another existing system uses laser excitation in a coaxial arrangement with a focused ultrasonic detection. However, the laser beam used in such a system is not focused. In fact, the laser beam is divergent because the positive acoustic lens functions as a negative optical lens. The negative optical lens actually broadens the optical beam. More importantly, such a system neither achieves nor claims optically defined lateral resolution, which is a key feature in the presently described embodiments.

The ability to image microstructures such as the microvascular network in the skin or brain cortex and monitor physiological functions of tissue is invaluable. One of the promising technologies for accomplishing this objective is photoacoustic microscopy. Current high-resolution optical imaging techniques, such as optical coherence tomography, can image up to approximately one transport mean free path of between 1 to 2 mm into biological tissues. However, such techniques are sensitive to the backscattering that is related to tissue morphology, and are insensitive to the optical absorption that is related to important biochemical information. Other known techniques such as confocal microscopy and multi-photon microscopy have even more restrictive penetration depth limitation and often involve the introduction of exogenous dyes, which with a few notable exceptions have relatively high toxicity. Acoustic microscopic imaging and spectroscopy systems are sensitive to acoustic impedance variations, which have little functional information about biological tissue and have low contrast in soft tissue. Other imaging techniques such as diffuse optical tomography or thermal wave microscopy have low depth to resolution ratio. Photoacoustic imaging as in embodiments of the invention provides high optical-absorption contrast while maintaining high penetration depth and high ultrasonic resolution. Moreover, because photoacoustic wave magnitude is, within certain bounds, linearly proportional to the optical contrast, optical spectral measurement can be performed to gain functional, i.e., physiological, information such as the local blood oxygenation level. However, increasing the resolution power beyond several tens of micrometers meets serious challenges. At ultrasonic frequencies required to achieve such resolution, which is above approximately 100 MHz, ultrasonic absorption in tissue gradually becomes proportional to the square of the ultrasonic frequency. Consequently, a resolution of several micrometers will have penetration depth of a few tens of micrometers that is much less than the penetration depth of other optical imaging techniques such as confocal microscopy. Embodiments of the present invention overcome the resolution limitation by using optical focusing to achieve high lateral resolution and ultrasonic detection to achieve axial resolution.

Although imaging of photothermal treatment of microvessels itself is biomedically significant, the capability of OR-PAM to image physiological and pathological changes in capillaries has broader applications. Other possible applications include imaging of vasodilation and vasoconstriction in stroke models, tumor angiogenesis, and tumor extravasations. Mouse ears were chosen as the initial organ to test OR-PAM because transmission optical microscopy could be used to validate the photoacoustic images. Since OR-PAM operates in reflection mode, it may be applied to many other anatomical sites.

Several alternative embodiments are possible. First, photoacoustic images may be acquired by scanning the optical-acoustic dual foci instead of the sample and the transducer container. Second, it is possible to scan only the optical focus within the acoustic focusing area to reduce the image acquisition time significantly. Third, by varying the excitation optical wavelength, physiological parameters such as hemoglobin oxygen saturation and blood volume may be quantified for in vivo functional imaging using endogenous contrast. Similarly, targeted exogenous contrast agents such as indocyanine green (ICG) and nanoparticles may be quantified for in vivo molecular imaging. Fourth, the acoustic coupling cube may be made to transmit photoacoustic waves ten times more efficiently without transformation from p-waves into sv-waves so that the SNR may be improved. Acoustic antireflection coating on the lens should further increase the SNR by approximately 10 dB.

When the optical focus is 100 µm below the tissue surface, the surface optical fluence is close to the ANSI safety limit of 20 mJ/cm2 in the visible spectral region. Although the ANSI standards regulate only the surface fluence, the spatial peak optical fluence is calculated at the focus in water, which is approximately 500 mJ/cm2. This focal fluence is still less than the experimentally observed damage threshold in live tissue. After the aforementioned improvements are implemented, the optical fluence may be reduced without affecting the SNR.

It will be understood that particular embodiments described herein are shown by way of illustration and not as limitations of the invention. The principal features in embodiments of this invention may be employed in various embodiments without departing from the scope of the invention. Those skilled in the art will recognize, or be able to ascertain using no more than routine experimentation, numerous equivalents to the procedures described herein. Such equivalents are considered to be within the scope of this invention and are covered by the claims.

All of the compositions and/or methods disclosed and claimed herein may be made and executed without undue experimentation in light of the present disclosure. While embodiments of this invention have been described in terms of preferred embodiments, it will be apparent to those of skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope and concept of the invention as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine, and/or combination of computing devices), a digital signal processor ("DSP"), an application specific integrated circuit ("ASIC"), a field programmable gate array ("FPGA"), or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although embodiments of the present invention have been described in detail, it will be understood by those skilled in the art that various modifications may be made therein without departing from the spirit and scope of the invention as set forth in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for noninvasively imaging a scattering medium, said method comprising:
    focusing at least one light pulse into a predetermined area inside an object using a focusing assembly;
    transforming absorbed optical energy into an acoustic wave, the acoustic wave emitted by the object in response to the light pulse;
    channeling the acoustic wave through a beam separation element that is either acoustically reflective and optically transparent or optically reflective and acoustically transparent;
    detecting the acoustic wave using at least one transducer positioned such that the transducer and the focusing assembly are coaxial and confocal; and
    creating an image of the predetermined area inside the object based on a signal generated by the transducer representative of the acoustic wave.

2. A method according to claim 1, wherein focusing at least one light pulse comprises focusing the at least one light pulse using a focusing optical system such that the at least one light pulse converges at a focal point of the transducer.

3. A method according to claim 2, wherein focusing at least one light pulse further comprises reducing the focal point of the focusing optical system to facilitate increasing a spatial resolution.

4. A method according to claim 1, wherein creating an image comprises recording and digitizing the received acoustic wave so that the predetermined area inside the object may be imaged.

5. A confocal photoacoustic imaging apparatus comprising:
- a focusing assembly configured to receive at least one light pulse and to focus the light pulse into an area inside an object, said focusing assembly comprising a beam separation element that is either acoustically reflective and optically transparent or optically reflective and acoustically transparent;
- at least one transducer configured to receive acoustic waves emitted by the object in response to the light pulse, said at least one transducer positioned such that said at least one transducer and said focusing assembly are coaxial; and
- a processor configured to record and process the received acoustic waves.

6. A confocal photoacoustic imaging apparatus according to claim 5, wherein said focusing assembly comprises an optical assembly of lenses and mirrors configured to focus the at least one light pulse on the object in such a way that a focal point of said focusing assembly coincides with a focal point of said at least one ultrasonic transducer.

7. A confocal photoacoustic imaging apparatus according to claim 5, wherein said focusing assembly focusing assembly is positioned on an XYZ translation stage in order to perform raster scanning along a surface of the object with simultaneous adjustment of an axial position of said apparatus to compensate for a curvature of the surface of the object.

8. A confocal photoacoustic imaging apparatus according to claim 5, wherein said focusing assembly comprises an optical microscope objective lens configured to focus the at least one light pulse into a nearly diffraction-limited point.

9. A confocal photoacoustic imaging apparatus according to claim 5, wherein said focusing assembly comprises an objective lens configured to form an image of a small pinhole on the area inside the object.

10. A confocal photoacoustic imaging apparatus according to claim 5, wherein said focusing assembly comprises an oscillating mirror configured to scan an optical focus rapidly within a larger focal area than a focal area of said at least one transducer.

11. A confocal photoacoustic microscopy system comprising:
- a laser configured to emit at least one light pulse;
- a focusing assembly configured to receive the at least one light pulse and to focus the light pulse into an area inside an object, said focusing assembly comprising a beam separation element that is either acoustically reflective and optically transparent or optically reflective and acoustically transparent;
- at least one ultrasonic transducer configured to receive acoustic waves emitted by the object in response to the light pulse, wherein said focusing assembly is further configured to focus the at least one light pulse on the object in such a way that a focal point of said focusing assembly coincides with a focal point of said at least one ultrasonic transducer; and
- an electronic system configured to process the acoustic waves and to generate an image of the area inside the object.

12. A confocal photoacoustic microscopy system according to claim 11, wherein said focusing assembly focusing assembly is positioned on an XYZ translation stage in order to perform raster scanning along a surface of the object with simultaneous adjustment of an axial position of said apparatus to compensate for a curvature of the surface of the object.

13. A confocal photoacoustic microscopy system according to claim 11, wherein said focusing assembly comprises an optical microscope objective lens configured to focus the at least one light pulse into a nearly diffraction-limited point.

14. A confocal photoacoustic microscopy system according to claim 11, wherein said focusing assembly comprises an objective lens configured to form an image of a small pinhole on the area inside the object.

15. A confocal photoacoustic microscopy system according to claim 11, wherein said focusing assembly comprises a single-mode optical fiber configured to emit a focused at least one light pulse.

16. A confocal photoacoustic microscopy system according to claim 11, wherein said focusing assembly comprises an oscillating mirror configured to scan an optical focus rapidly within a larger focal area than a focal area of said at least one transducer.

17. A confocal photoacoustic microscopy system according to claim 11, wherein said electronic system is configured to record the acoustic waves and to display the recorded acoustic waves versus a corresponding position of said focusing assembly in order to generate the image.

18. A confocal photoacoustic microscopy system according to claim 17, wherein said electronic system comprises a motor controller configured to synchronize data acquisition and object scanning with the at least one light pulse at programmed locations of the laser focus with respect to the object.

* * * * *